United States Patent
Vollmer

(10) Patent No.: US 11,352,597 B2
(45) Date of Patent: Jun. 7, 2022

(54) MEDICAL DEVICE FOR THE SELECTIVE SEPARATION OF A BIOLOGICAL SAMPLE

(71) Applicant: MY123BABY MEDICAL LIMITED, Dublin (IE)

(72) Inventor: Marion Vollmer, Unterhaching (DE)

(73) Assignee: MY123BABY MEDICAL LIMITED, Dublin (IE)

( * ) Notice: Subject to any disclaimer, the term of this patent is extended or adjusted under 35 U.S.C. 154(b) by 571 days.

(21) Appl. No.: 15/763,644

(22) PCT Filed: Sep. 28, 2016

(86) PCT No.: PCT/EP2016/073133
§ 371 (c)(1),
(2) Date: Mar. 27, 2018

(87) PCT Pub. No.: WO2017/055361
PCT Pub. Date: Apr. 6, 2017

(65) Prior Publication Data
US 2018/0282676 A1 Oct. 4, 2018

(30) Foreign Application Priority Data

Sep. 28, 2015 (DE) .................. 102015116391.8

(51) Int. Cl.
*C12M 3/00* (2006.01)
*B01L 3/00* (2006.01)
(Continued)

(52) U.S. Cl.
CPC ....... *C12M 21/06* (2013.01); *B01L 3/502753* (2013.01); *C12M 47/02* (2013.01);
(Continued)

(58) Field of Classification Search
CPC ..... C12M 21/06; C12M 47/02; C12N 5/0612; B01L 3/502753; B01L 2300/0681;
(Continued)

(56) References Cited

U.S. PATENT DOCUMENTS 4,759,344 A 7/1988 Wang
5,427,946 A 6/1995 Kricka et al.
(Continued)

FOREIGN PATENT DOCUMENTS

CN 104099293 A 10/2014
EP 1401342 B1 3/2004
(Continued)

OTHER PUBLICATIONS

Anat Bahat, et al., Thermotaxis of Human Sperm Cells in Extraordinarily Shallow Temperature Gradients Over a Wide Range, PLoS ONE, Jul. 2012, vol. 7, Issue 7.
(Continued)

*Primary Examiner* — Dennis White
(74) *Attorney, Agent, or Firm* — Millman IP Inc.

(57) ABSTRACT

The present invention provides a medical device and a method for the selective separation of a biological sample of a mammal into a first portion and a second portion. It comprises a first layer comprising a first reservoir for receiving the biological sample and for retaining the first portion of the sample, and a second layer comprising a second reservoir for receiving the second portion of the sample. Between the first layer and the second layer a third layer is provided, wherein the third layer comprises a plurality of channels configured to provide a fluid communication between the first reservoir and the second reservoir. Furthermore, between the first layer and the second layer a fourth layer adjacent to the third layer is provided, wherein the fourth layer comprises and/or is configured as a separa-
(Continued)

tion layer. At least the third and fourth layer are configured to selectively separate the biological sample between the first reservoir and the second reservoir into the first portion and the second portion of the sample. According to the invention, the layers are to be understood to be stackable in a substantially vertical plane, forming a three-dimensional layered structure.

28 Claims, 10 Drawing Sheets

(51) Int. Cl.
  *C12M 1/00* (2006.01)
  *C12N 5/071* (2010.01)

(52) U.S. Cl.
  CPC .... *C12N 5/0612* (2013.01); *B01L 2200/0652* (2013.01); *B01L 2300/0681* (2013.01); *B01L 2300/0887* (2013.01); *B01L 2300/1805* (2013.01); *B01L 2400/06* (2013.01); *B01L 2400/0638* (2013.01); *B01L 2400/0666* (2013.01)

(58) Field of Classification Search
  CPC ..... B01L 2300/1805; B01L 2400/0666; B01L 2400/0638; B01L 2200/0652; B01L 2300/0887; B01L 2400/06
  See application file for complete search history.

(56) References Cited

U.S. PATENT DOCUMENTS

| | | | |
|---|---|---|---|
| 5,744,366 | A | 4/1998 | Kricka et al. |
| 5,866,354 | A | 2/1999 | Froman |
| 2006/0144707 | A1 | 7/2006 | Landers et al. |
| 2009/0123961 | A1 | 5/2009 | Meyvantsson et al. |
| 2010/0291535 | A1 | 11/2010 | Yao et al. |
| 2010/0300882 | A1 | 12/2010 | Zhang et al. |
| 2011/0091932 | A1 | 4/2011 | Plewa et al. |
| 2012/0328488 | A1 | 12/2012 | Puntambekar et al. |
| 2013/0264266 | A1 | 10/2013 | Shick et al. |
| 2014/0323911 | A1 | 10/2014 | Sloan et al. |
| 2015/0079676 | A1 | 3/2015 | Wright et al. |
| 2015/0140655 | A1 | 5/2015 | Nosrati et al. |

FOREIGN PATENT DOCUMENTS

| | | |
|---|---|---|
| EP | 1432787 B1 | 6/2004 |
| EP | 2682747 A1 | 1/2014 |
| WO | 200160968 A1 | 8/2001 |
| WO | 2002102968 A1 | 12/2002 |
| WO | 2004108011 A1 | 12/2004 |
| WO | 2012032165 A1 | 3/2012 |
| WO | 2013016477 A1 | 1/2013 |
| WO | 2013040428 A1 | 3/2013 |
| WO | 2013129947 A1 | 9/2013 |
| WO | 2014053237 A1 | 4/2014 |

OTHER PUBLICATIONS

Lopez-Garcia, et al., Sperm motion in a microfluidic fertilization device, Biomed Microdevices (2008), May 3, 2008, pp. 709-718, Springer Science + Business Media, LLC.

Huang, Hong-Yuan, et al., Motile Human Sperm Sorting by an Integrated Microfluidic System, Journal of Nanomedicine & Technology 2014, May 25, 2014, pp. 1-6, vol. 5, Issue 3.

International Search Report for International Application No. PCT/EP2016/073133, dated Dec. 21, 2016.

Written Opinion of the International Searching Authority for International Application No. PCT/EP2016/073133, dated Dec. 21, 2016.

Examination Report from German Patent Office, dated Jun. 7, 2016.

MEDICAL DEVICE FOR THE SELECTIVE SEPARATION OF A BIOLOGICAL SAMPLE

TECHNICAL FIELD

The present invention relates to a medical device and a method for separating a biological sample of a mammal, preferably semen, into a first and second portion. In particular, the invention relates to a medical device and a method for a motility-based separation of biologically active sperm cells for the enrichment of qualitative sperm.

TECHNOLOGICAL BACKGROUND

Infertility is an increasing phenomenon leading to prevalence rates ranging between 11 and 16 percent in both industrialized and developing countries worldwide. Couples coping with these problems in many cases seek medical assistance to artificially enhance their pregnancy and live birth potential. Known technologies include e.g. Assisted Reproductive Technologies (ART) and Intrauterine Insemination (IUI). Unfortunately, the success rate of ARTs is generally only about 20 to 30 percent and often requires 4 to 5 fertilization rates. Furthermore, assisted reproduction had mainly focused on increasing the female reproduction potential, focusing primarily on egg retrieval and cultivation due to the common misbelief that sperm quality had no or not a substantial effect on fertility. The subsidiary role of sperm has only recently become a topic of interest.

About 40 to 50 percent of fertility issues are due to male infertility. Accordingly, ARTs influence both the success rate of pregnancy and offspring health. In vivo and particularly in situ treatment of infertility is rarely possible. Since ART comprises both In Vitro Fertilization (IVF) and Intra-Cytoplasmic Sperm Injection (ICSI), ART plays an important role due to the increasing number of IVF treatments. In IVF, an oocyte is incubated with an aliquot of 50,000 sperm cells from an initial sample comprising an order of 100 million sperm cells. Such numbers are typically required for droplet based IVF, wherein egg cells are surrounded by a specific number of sperm cells that possibly fertilize the egg while for ICSI a single sperm cell is selected and directly injected into an oocyte. In contrast, for human IUI, about 5 to $50 \times 10^6$ sperm cells are typically used. For all treatments, sperm separation and/or enrichment are performed. Hence, selection of the most fertile sperm is essential for the success rates of ARTs.

In some current techniques, due to time limitations or restrictions, no actual sperm separation, but rather only a sperm purification process is performed. The sperm purification process typically only cleans the seminal fluid away from the sperm. This means that such sperm preparation methods may not sort the most fertile sperm from a sample. Semen preparation to increase the quality of sperm is generally based on current WHO standards, i.e. centrifugation techniques and swim-up assays based on sedimentation and migration. However, while high density gradient centrifugation and/or swim-up assays provide for an increased concentration and retrieval of sperm cells and have been found to generally select sperm populations with increased DNA integrity, the quality of the sperm cells is often (still) impaired. Furthermore, said methods do not resemble the natural in vivo process and the selected sperm population is often contaminated with poorly motile sperm and somatic cells (e.g. leukocytes), generally requiring a visual inspection. In addition, the selected sperm population may suffer iatrogenic injury (e.g. oxidative injury) due to centrifugation and/or prolonged and repeated processing, particularly reducing DNA quality. The occurring DNA damage in sperm cells directly correlates A) to an insufficient increase of fertility or even fertilization failure, and B) often leads to miscarriages, while the success rate of ART is accordingly reduced. Such methods hence do not provide a desirable outcome.

Furthermore, known selection techniques often depend on professional skills and technician experience in selecting sperm and are based on multi-step methods, rendering the method potentially error-prone. In addition, centrifugation also requires both expensive equipment and materials and is time-extensive, limiting infertility services to middle and high income households.

Despite these adverse effects, clinical spermatozoa preparation techniques have not significantly improved in the past 20 years. As an alternative for spermatozoa preparation a microfluidic-based method may provide an outcome to address this lack of improvement. Microfluidic approaches are well suited to cell manipulation and have been adapted to select or manipulate sperm based on e.g. motility, chemotaxis, optical forces, and electrophoresis. For example, from the patent application US 2011/0091932 A1 an automated extraction method using optical tweezers is known. However, such methods are not applicable for e.g. sperm separation techniques, wherein a large number of cells is required and furthermore require professional skill for handling. By the same token, from the patent application US 2009/0123961 A1 a method for testing of chemotaxis is known using a fluid gradient, which furthermore provides no barriers and may hence not be applicable to or effective for highly motile cells.

Hence, in most cases, the complexity of using microfluidic devices and the need for supporting infrastructures decrease effectiveness while increasing costs and hence currently do not allow for a clinical implementation, scaling, and/or commercialization. Moreover, the low sample volume characteristic of microfluidics proves to be a disadvantage in the context of sperm selection due to the inherent milliliter-scale size of human samples.

Accordingly, a need exists to improve semen processing and sperm separation to treat male infertility, preferably while improving scalability and processing time.

SUMMARY OF THE INVENTION

It is an object of the present invention to overcome the problems and limitations of the current technologies by providing a medical device and a method for the selective separation of a biological sample of a mammal into a first portion and a second portion.

In a first aspect, the medical device for the selective separation of a biological sample of a mammal comprises a first layer comprising a first reservoir for receiving the biological sample and for retaining the first portion of the sample, and a second layer comprising a second reservoir for receiving the second portion of the sample. Between the first layer and the second layer a third layer is provided, wherein the third layer comprises a plurality of channels configured to provide a fluid communication between the first reservoir and the second reservoir. Furthermore, between the first layer and the second layer a fourth layer adjacent to the third layer is provided, wherein the fourth layer comprises and/or is configured as a separation layer. At least the third and fourth layer are configured to selectively separate the biological sample between the first reservoir and the second reservoir into the first portion and the second portion of the sample. The layers are to be understood to be stackable in a substantially vertical plane, forming a three-dimensional layered structure.

Furthermore, the fourth layer may comprise a porous structure and is preferably configured to selectively separate the biological sample between the first reservoir and the second reservoir into the first portion and the second portion of the sample. Accordingly, at least the third and fourth layer facilitate and/or direct the selective separation of the biological sample. The fourth layer may be either disposed between the third layer and second layer or between the first and third layer. Preferably, the fourth layer is disposed between the first layer and the third layer so that it may e.g. facilitate a primary selection or barrier for the first portion. Further separation and/or selection may then occur, and potentially more efficient, in the plurality of channels of the third layer. Accordingly, such an arrangement would have a synergistic effect. Alternatively, a configuration, wherein the fourth layer is disposed between the third layer and the second layer may e.g. reduce the occurrence of (partial) clogging of channels by e.g. sediment, which would impair movement of the second portion towards the second reservoir.

Alternatively, the biological sample may comprise other eukaryotic cells or prokaryotic cells, e.g. yeast or *E. coli*.

The biological sample may be a fluid and/or semi-solid sample. Preferably, the sample comprises semen comprising a biologically active component, wherein the biologically active component is separated from the first reservoir. The fluid and/or semi-solid sample may be either an untreated or treated sample. For example, the sample may be directly provided in the first reservoir or mixed with a buffer to e.g. optimize homogeneity and physiological parameters prior to providing the sample in the first reservoir. Furthermore, the sample may be adjusted until e.g. a desired volume and/or viscosity is achieved. The term semi-solid sample is to be understood to include e.g. turbid medium, slabs, gel-like structures, suspensions, dispersions, colloids, structures with high and/or varying viscosities, and/or tissue of a mammal. The latter may e.g. be obtained from larger mammals, wherein non-invasive methods to obtain the sample are not applicable. The medical device may be used for research purposes, i.e. the sample may be used for diagnostic purposes such as e.g. chemotaxis assays.

In particular, the biologically active component comprises sperm, preferably spermatozoa. Other biologically active components may comprise e.g. peptides, hormones, cytokines, chemokines, and/or other mammalian cell types such as e.g. myeloid cells, lymphoid cells, and/or cells of the nervous system. Alternatively, or in addition, the medical device may be configured to prevent, inhibit, or impair separation of at least a part of the biologically active component. In other words, a part of the biologically active component may be retained in the first reservoir during a separation. For example, parts that may be retained may comprise e.g. seminal plasma, chaperones, heat-shock proteins, enzymes, and/or ligands.

The plurality of channels of the third layer may have an angular orientation relative to the first layer and/or the second layer of at least 60 degrees, preferably perpendicular to the first layer and/or second layer. The first and second layer are preferably parallel to each other, however, may also have a converging, diverging, and/or concentric orientation.

At least one of the layers of the medical device may furthermore be configured for directing movement of a biologically active component in the biological sample from the first reservoir to the second reservoir. Directing of movement of the biologically active component may e.g. facilitate transfer, migration, and/or separation of a portion of the sample from the first reservoir to the second reservoir. For example, the biologically active component may comprise spermatozoa.

In particular, the plurality of channels of the third layer may be configured for directing movement of a biologically active component in the biological sample. Preferably, each channel of the third layer comprises a surface structure that promotes and/or supports motility of a biologically active component in the biological sample or that selectively promotes and/or supports a biologically active motile component in the biological sample. For example, the surface structure may impair or facilitate adhesion, e.g. by comprising a specific surface tension, roughness, and/or coating. Furthermore, the surface structure may be formed to direct and/or guide a motile biologically active component, e.g. a spermatozoon, in a specific direction, thereby facilitating a separation of the portion of the sample from the first reservoir into the second reservoir.

Preferably, the plurality of channels of the third layer is non-linear and/or comprises an arrangement of edges. Said non-linear shape and/or arrangement of edges may be provided in an orientation corresponding to the first layer, second layer, and/or the channels from the first layer to the second layer. For example, edges may be provided at an opening of the channels at the first reservoir and/or the second reservoir, e.g. in a substantially horizontal plane, and/or may be provided along the channels in e.g. a substantially perpendicular, vertical, or Z-plane orientation.

Furthermore, the plurality of channels of the third layer may comprise a substantially meandering, sinuous, helical, and/or zig-zag structure. Said structure may be provided in an orientation corresponding to the first layer, second layer, and/or the channels from the first layer to the second layer. For example, the channels may comprise a zig-zag structure in an orientation corresponding to the first layer, i.e. a substantial horizontal plane, while preferably comprising a conical or pyramid shape in a substantially perpendicular orientation, i.e. a vertical or Z-plane. The channels of the third layer may furthermore comprise an inner thread, e.g. comprise continuous helical grooves at the wall of the channels in a substantially perpendicular orientation, i.e. a vertical or Z-plane. The walls of the plurality of channels may furthermore comprise a surface roughness adapted to facilitate the separation of the second portion into the second reservoir. For example, the surface roughness may impair adherence yet facilitate motility and/or direct the second portion.

The configuration of the plurality of channels may be particularly beneficial for the separation of spermatozoa from the sample in the first reservoir into the second reservoir. For example, since spermatozoa generally prefer to swim along walls, a characteristic called natural boundary-following swimming behavior or "corner-swimming behavior", and particularly choose a corner that guides them through a (microfluidic) channel, the provision of non-linear structures and/or the arrangement of edges may be implemented to direct their movement.

The specific configuration of the plurality of channels may hence facilitate and direct the movement of motile cells into a desired direction. This at least has the advantage that e.g. sperm cells with high motility, corresponding to e.g. high DNA integrity, and strong corner-swimming behavior may be effectively directed into the second reservoir. In contrast, sperm cells with low motility and comprising e.g. random motion, turbulent motion, and/or Brownian motion, may, just as sediment, not be effectively separated and thus retain within the first reservoir. Accordingly, the configuration, e.g. the shape, orientation, and/or the length of the plurality of channels may be adapted to a duration of the separation and/or a level of enrichment of the second portion, e.g. high quality sperm cells, to be achieved. Thus, such structures may facilitate the separation of sperm from the first reservoir into the second reservoir. Such an approach does not require complicated channel systems in the micrometer range.

In addition, or alternatively, the plurality of channels of the third layer is shaped such that their width at the first layer is larger than their width at the second layer. For example, the width of the channels in a substantially vertical plane is larger at the bottom of the channels when compared with the top of the channels. The plurality of channels may hence comprise a larger width at the fourth layer, if the fourth layer is positioned between the third layer and the first layer, compared with the width at the second layer. The width of the channels may furthermore decrease gradually, successively, or interval-based towards the second layer. The channels may hence be shaped to comprise e.g. a substantially conical, cylindrical and/or polygonal shape.

Such narrowing of the channels prevents or at least reduces the occurrence of e.g. sperm with a random swimming pattern to accumulate at the top of the channels or in the second reservoir. Furthermore, the occurrence of back-swimming is reduced. Accordingly, narrowing may facilitate that sperm exerting a natural boundary-following-swimming behavior and hence comprising an excellent DNA quality accumulate in the second reservoir.

Accordingly, the medical device according to the invention mimics the in vivo process in the fallopian tube, simulating the natural conditions of the female body, e.g. by combining a micro-network with narrowing boundary structures and a physiological buffer, hence providing a more natural method.

The second reservoir may comprise at least one side, bottom, and/or top surface having a rounded, cylindrical, semicircular, conical, U-shaped, and/or polygonal shape, wherein preferably the sides, bottom and top surface are shaped to provide a retaining structure for the second portion of the sample and/or to prevent convection and/or turbulence during flow of the second portion of the sample. Accordingly, the second reservoir may be configured to direct and retain spermatozoa based on its shape. For example, a combination of side or wall configuration of the second reservoir may direct and/or enrich spermatozoa with natural boundary-following swimming behavior into a corner, e.g. at the top of the second reservoir, wherein the shape of the corner prevents back-swimming into the channels. Accordingly, the shape of the second reservoir directs and retains the spermatozoa into the second reservoir, i.e. substantially preventing back-swimming and forming a "trap". The walls may e.g. comprise a semi-circular shape towards the top of the second reservoir, wherein the top of the reservoir may comprise a substantially polygonal or edged shape, e.g. a substantially triangular shape, to retain or at least substantially retain the second portion of the sample in the second reservoir.

The second reservoir, in particular the angle of a polygonal shape or edge of e.g. the top of the second reservoir, may be chosen to prevent the formation or build-up of a fluid meniscus. For example, the surface roughness and/or the angle between the walls may be chosen such that upon a removal of the second portion of the sample, e.g. to obtain enriched high quality spermatozoa, a negligible number of or no spermatozoa are retained at the surface of the walls due the occurring flow. Preferably, no vortices and/or convection are generated due to such a flow, i.e. a substantially laminar flow is generated. Furthermore, narrowing the second reservoir, e.g. towards the top, allows retaining sperm in a compartment or corner of the reservoir and prevents or reduces the occurrence of back-swimming into the plurality of channels. In addition, reducing the dimensions allows having a reservoir with a smaller volume and a smaller or compact design of the medical device. Accordingly, the dimensions may be varied to provide a scalable medical device.

The first reservoir may be formed as a channel or a plurality of channels, wherein the channel or plurality of channels preferably is non-linear and/or comprises a substantially meandering, sinuous, helical, pedigree, circular, ellipse, U-shaped, serpentine-shaped, and/or zig-zag structure, and/or comprises no sharp edges. Said structure may extend in an orientation corresponding to the first layer, i.e. in a substantially horizontal plane. In particular, a U-shaped or similar shaped channel is preferred to reduce the occurrence or generation of vortices, shear flow, velocity changes, and/or convection due to a flow, i.e. to provide a substantially laminar flow. A U-shape may furthermore be preferred to allow or facilitate complete replacement of buffer in the first reservoir by semen and/or may reduce the occurrence and/or accumulation of bubble formation during e.g. injection.

Furthermore, the first reservoir and/or the second reservoir may be configured to minimize convection, fluid resistance, and/or turbulent flow when the biological sample is flowed. For example, the reservoir may comprise a diameter and/or surface roughness that facilitate a laminar flow when a flow occurs in the reservoir and preferably reduces the occurrence of vortices.

The fourth layer comprising and/or configured as separation layer may comprise a porous structure at the entire surface or at a surface corresponding to a top surface of the first reservoir or the plurality of channels of the third layer. Preferably, the porous structure is provided continuously, as a multi-hole array, or at a predefined interval, and the positioning of the pores substantially coincides with the opening of the plurality channels of the third layer at the first layer or the second layer. For example, if the fourth layer is arranged between the first layer and the third layer, the pores may align with openings of the plurality of channels of the third layer at the first layer, thereby providing a fluid communication between the first reservoir and the plurality of channels. The pores are particularly fully aligned with all openings of the plurality of channels, however, partial misalignment may occur, leading to a partial block of a negligible number of channels. This may e.g. occur when a continuous pore structure of the fourth layer is used, however, the spacing between said pores may be minimal such that even in the case of misalignment the fluid communication between the plurality of channels and the reservoir is not significantly impaired. Furthermore, a mask may be provided between the first layer and the fourth layer and/or between the third layer and the fourth layer to align the pores with the first reservoir or plurality of channels of the third layer. Accordingly, the occurrence of misalignment is prevented, negligible, or at least reduced.

Preferably, the separation layer of the fourth layer comprises or is configured as a membrane, wherein the membrane comprises a biologically inert or active material, preferably cellulose-, paper-, and/or polymer-based. The use of a membrane, preferably comprising a continuous porous structure, has at least the advantage that alignment issues with the plurality of channels of the third layer may be reduced and fabrication of the medical device is simple and cost effective. Furthermore, said membranes are widely used in the medical field and hence do not cause biocompatibility issues.

The separation layer may furthermore be configured to minimize the occurrence of convection and/or pressure difference within and/or between at least the second and third layer. Preferably, the separation layer is configured such that furthermore no convection and/or pressure difference occurs between the first reservoir and the second reservoir. In particular, the separation layer may comprise a porous structure, wherein the porous structure is configured to minimize the occurrence of convection and/or pressure difference, preferably due to the pore size.

In cases wherein the separation layer comprises a pore structure, the pore size may comprise between 20 and 500 μm, preferably between 50 and 200 μm, in particular 100 μm. Said sizes may have a nominal deviation, i.e. the pore size may comprise up to 10 percent error due to fabrication and/or processing. Alternatively, the pore sizes may be varied along the surface of the separation layer, e.g. to adapt potential fluctuations when a flow occurs in the reservoir.

The layers may furthermore be configured such that the device is rotatable during loading of the first reservoir with the biological sample to substantially orientate the first layer in a gravitational plane. Such orientation may also be provided during the separation of the second portion from the first reservoir into the second reservoir. Accordingly, the second portion of the biological sample is separated in a horizontal plane, e.g. motile spermatozoa swim from the first reservoir into the second reservoir in a substantially horizontal direction. The term substantially is to be understood such that the device may be tilted and/or rotated along the gravitational plane yet generally comprises a vertical orientation. Such configuration and orientation at least has the advantage that the occurrence of bubble formation may be reduced and allows for an extent of flexibility during loading of the reservoir with the biological sample.

At least the second reservoir, the separation layer, and the plurality of channels in the third layer may furthermore comprise a fluidic buffer. Preferably, said components of the medical device comprise the buffer prior to loading of the first reservoir with a biological sample. Optionally, the first reservoir may also comprise a fluidic buffer prior to loading of the first reservoir with a biological sample. In this case, the loading of the first reservoir with a biological sample replaces the buffer in the first reservoir. Alternatively, the buffer may also be provided in the second reservoir, the separation layer, and the plurality of channels in the third layer after loading of the first reservoir with a biological sample.

The buffer may be any medical grade buffer, preferably an aqueous and/or low-viscosity buffer. The buffer at least has the advantage that a fluid communication is established in the medical device between the first reservoir and the second reservoir such that e.g. sperm cells can move and/or be separated from the first reservoir into the second reservoir. Furthermore, the buffer may affect the surface tension of the plurality of channels, thereby directing movement and/or supporting motility of spermatozoa. In addition, the buffer may be mixed with the biological sample prior to loading of the first reservoir to reduce the viscosity of the biological sample. This may also be facilitated by addition of an additional component. For example, a low-viscosity buffer may comprise a component to facilitate the shedding of seminal plasma, thereby facilitating the liquefaction of semen for loading purposes and increasing the motility of spermatozoa.

Dimensions of the medical device may be varied to provide a patient-specific or species-specific application and/or optimization. For human applications, the first reservoir preferably comprises a volume between 0.5 and 5 mL, whereas the second reservoir preferably comprises a volume between 100 μL and 1 mL, preferably 500 μL. These values indicate optimal and/or maximal values to accommodate a corresponding biological sample, either untreated or treated, as described above.

The plurality of channels of the third layer preferably comprises a length between 2 and 15 mm, whereas the fourth layer preferably comprises a length between 100 μm and 1 mm, preferably between 400 μm and 600 μm, in particular 500 μm. Said lengths are to be understood to comprise the lengths in a substantially vertical plane, i.e. in an orientation between the first layer and the second layer. By the same token, these values indicate optimal and/or maximal values, preferably adapted to a desired separation time and/or motility and/or size of spermatozoa.

The above dimensions only indicate preferable values as desirable for applications for a single human patient. However, depending on species and/or infertility grade or problem, other dimensions may be chosen. Accordingly, the medical device may be scaled up or down, e.g. particularly larger sizes and volumes may be chosen or series-connected medical devices may be provided to accommodate a bovine or equine sample.

Loading of a biologic sample is often facilitated by injection or perfusion. Accordingly, the first and second reservoir preferably each comprises an inlet and an outlet, wherein preferably at least one inlet and/or outlet can be selectively opened and/or closed. Preferably, an inlet and/or outlet of each reservoir may be adapted to connect and/or receive a second medical device, preferably a third reservoir, a syringe, and/or catheter. In particular, the inlet and/or outlet may be configured as a widely used luer connection to provide a fluid communication with a medical application device.

Alternatively, or in addition, an inlet and/or outlet of each reservoir may be configured to minimize convection, fluid resistance, and/or turbulent flow when the biological sample is removed from the second reservoir. For example, a luer connection or a modification thereof may also minimize convection, fluid resistance, and/or turbulent flow.

Furthermore, the first and/or second reservoir may comprise a valve arrangement, wherein the valve arrangement preferably minimizes the occurrence of gas and particularly bubble accumulation in the respective reservoir. For example, an outlet of the first reservoir may comprise a valve arrangement to allow accumulating gas, e.g. during loading of the biological sample, to exit the first reservoir, thereby also preventing bubble accumulation in other layers such as e.g. the channels of the third layer. Furthermore, an inlet of the first reservoir may comprise a valve arrangement such as a bubble catcher to prevent bubble accumulation in the first reservoir during loading of the biological sample. By the same token, an inlet or outlet of the second reservoir may comprise a valve arrangement such that during removal of the second portion of the biological sample from the second reservoir no pressure or negative pressure such as a vacuum is built. This at least has the advantage that potential jamming or malfunctioning is reduced and the usability is accordingly increased.

Alternatively, or in addition, the first and/or second reservoir may comprise a flow constriction means to control a flow of the biological sample within the reservoir. Such a flow constriction means may be e.g. a pressure valve or porous plug to e.g. ensure a laminar flow, a maximal volume, and/or maximal flow rate. Preferably, such a flow constriction means is combined in or with the valve arrangement to reduce the number of components, increase robustness and usability and allow for a compact design.

The plurality of channels of the third layer may comprise a closing means for selectively and/or substantially sealing of the third layer at the first and/or second layer, which is configured to prevent convection from the plurality of channels of the third layer to the second reservoir when a flow of the second portion of the biological sample occurs in the first or second reservoir. Preferably, the closing means comprises a microfluidic valve, a sealable membrane, a solenoid valve, and/or diaphragm valve. In particular, the closing means may be configured to be selectively closed in at least one flow direction. This at least has the advantage that when e.g. a flow occurs during loading of the biological sample or during removal of the second portion of the sample from the second reservoir, no or no significant amount of unwanted components are transferred into the second reservoir. For example, the second portion may ideally only comprise spermatozoa with high motility to ensure the presence of sperm with high quality DNA. These cells actively migrate from the first reservoir to the second reservoir, whereas non-motile sperm and/or sediment accumulate in the first reservoir and or lower portion of the plurality of channels in the third layer due to gravity and/or random swimming behavior. A closing means such as a microfluidic valve would e.g. ensure that during removal of the second portion of the sample from the second reservoir, no convection occurs so that e.g. non-motile sperm is retained in the first reservoir and/or plurality of channels and hence does not enter the second reservoir.

The medical device may be made of any biocompatible material, preferably a thermoplastic polymer, in particular polycarbonate. The material may further be chosen such that it can be sterilized, preferably by means of alcohol incubation, autoclaving, and/or plasma treatment. Accordingly, the medical device comprises a medical grade and clinically approved material. Alternatively, a combination of materials may be used, for example, different materials may be chosen and/or more applicable for the relevant layer.

Furthermore, the medical device may be made of a single piece. Accordingly, the medical device may be produced from a single piece, but more preferably is made of several components that are joined together to form an integral single piece. This is particularly preferable for handling purposes, practicability, and user friendliness.

Alternatively, the layers may also be provided as a modular device. Accordingly, patient-specific and/or purpose-specific configurations of the respective layers may be chosen.

The different layers may be combined by methods known in the art, e.g. by positive locking, form closure, pressure, biocompatible adhesives, pressure, compression, and/or sealing membranes, or a combination thereof.

The medical device may be preferably be configured to be portable, preferably configured as a home-care product. In particular, configuration as a single piece that is portable increases the user flexibility, thereby no longer requiring the patient to attend a clinical facility but perform the treatment at a more familiar atmosphere such as at a patient's home. However, the increased mobility also facilitates its use in a clinical facility due to e.g. reducing storage costs, ease of transportation, and increased flexibility of treatment rooms.

The medical device may furthermore be configured as a single-use product. Accordingly, cumbersome cleaning and sterilization may no longer be required, speeding up the treatment and further reducing treatment costs.

Preferably, the medical device may be produced according to a method or process of hot embossing, sintering, 3D printing, injection molding, casting, curing, soft lithography, die-cutting, and/or applied coronary or plasma treatment.

The medical device at least has the advantage that a simple, easy to use yet robust device is provided, wherein the microfluidic approach allows for an efficient, cost-effective and fast separation of sperm. Due to the intrinsic sperm motility, sperm with high quality can be efficiently separated and/or retrieved for further treatment. Additionally, both due to the microfluidic approach as well as the specific design of the plurality of channels, sperm cells are not subjected to stress when compared with widely used centrifugation techniques. Instead, they rather mimic the in vivo process in the fallopian tube, simulating the natural conditions of the female body, e.g. by using a low-viscosity, physiological buffer and a micro-network, hence providing a more natural method. The scalable design furthermore allows its implementation in clinical facilities and at home and may be likewise implemented for other animal applications, e.g. for breeding using bovine or equine sperm samples.

According to another aspect of the invention, a system for the selective separation of a biological sample of a mammal into a first portion and a second portion is provided. The system may comprise at least a biological sample and at least one medical device as described above. Furthermore, it may comprise at least a medical application device for loading the first reservoir of the at least one medical device with the biological sample and a second medical application device for removing a second portion of the biological sample from the second reservoir of the at least one medical device and configured to administer the second portion of the biological sample to a patient. Such medical application devices may e.g. comprise a syringe, a reservoir, and/or a catheter such as e.g. an intrauterine insemination catheter.

Preferably, the system comprises a heating unit for maintaining the system at a desired temperature, preferably between 25 and 37 degrees Celsius. In addition, or alternative, the system may comprise an incubator, wherein preferably physiological conditions are mimicked. In particular, physiological conditions such as oxygenation, carbon dioxide and/or nitrogen concentrations are considered. Other factors such as e.g. humidity may also be controlled. The system may also comprise a separate oxygenator.

The system may also comprise a fastener or fixation means to e.g. ensure stability and/or prevent the medical device from being moved or tilted during separation. The fixation means may also be adapted to be separated from the medical device to facilitate fixation of other components in the system. For example, the fixation means may be used to fixate the biological sample during a pre-incubation phase for liquefaction, i.e. to fix the biological sample to a heating plate and/or low-speed shaker, or to fix the biological sample to a body part, thereby keeping the biological sample at body temperature. The fixation means may comprise any means known in the art, e.g. elastic or rubber bands, Velcro straps, clamps, tie-wraps, or the like. The medical device may also be placed and fixed into a base, which may e.g. house and heat the medical device during pre-incubation and separation and may also provide a mechanical arrangement to provide vibrations, e.g. a relay-based or electromagnetic arrangement.

The system may furthermore comprise a display and a clock function, e.g. to indicate a desired time and/or a current time of pre-incubation or separation. The display may hence provide a countdown function and/or an alarm. The alarm may be acoustic, visual, haptic, and/or tactile. The display may be any display known in the art, e.g. LCD or LED based, and may be driven by a processor, a memory and an electrical energy storage device such as e.g. a battery.

To guide the user through the required subsequent steps, the system may furthermore comprise functional indicators. The system may hence provide labels, colors, numbers, and/or text. For example, the colors may be provided to indicate a correct or appropriate insertion and/or corresponding components, whereas text and/or numbers may indicate a correct application order. The system may furthermore provide a positioning indicator, e.g. a level, to allow a user to ensure a correct alignment during separation. Preferably, the functional indicators are provided in or on the medical device, i.e. forming an integrated medical device. Said functions may also be provided by the display described above.

According to another aspect of the invention, a method for the selective separation of a biological sample of a mammal with the above described medical device is provided. According to the method, at least the second reservoir, the separation layer, and the plurality of channels of the third layer are loaded, flushed, incubated, and/or mixed with a buffer, after which the first reservoir is loaded with a biological sample of a mammal, wherein the second reservoir is fluidly sealed. The first reservoir may optionally be filled with a buffer prior to the loading of the first reservoir with the biological sample. The biological sample then replaces the buffer in the first reservoir during loading. Alternatively, the second reservoir, the separation layer, and the plurality of channels of the third layer are loaded with a buffer after loading of the first reservoir with a biological sample. In any case, a fluid communication is provided between the first reservoir and the second reservoir after the loading of the first reservoir with the biological sample.

During the loading of the first reservoir with the biological sample the plane of the medical device may furthermore be adjusted, e.g. to prevent the accumulation of gas in at least the first reservoir. For example, the medical device may be rotated such that the first reservoir has an orientation that is substantially aligned with the gravitational plane. Bubble formation may hence be prevented or at least reduced. When the first reservoir is configured as a channel, in particular a serpentine-shaped channel, the medical device may be accordingly rotated during the loading of the first reservoir. The rotation hence furthermore allows for an extent of flexibility and user friendliness during loading of the reservoir with the biological sample.

The first reservoir is then fluidly sealed without establishing a pressure gradient between the first reservoir and the second reservoir. The biological sample is then selectively separated between the first reservoir and the second reservoir into a first portion and a second portion. Preferably, the plurality of channels of the third layer are thereby substantially oriented towards or aligned with a plane of gravitational force. Alternatively, a horizontal orientation, as described above during loading, may also be provided during the separation of the second portion from the first reservoir into the second reservoir. Accordingly, the second portion of the biological sample is separated in a horizontal plane, e.g. motile spermatozoa swim from the first reservoir into the second reservoir in a substantially horizontal direction.

Preferably, the selective separation occurs due to biological activity, preferably motility, and/or gravitational force. For example, spermatozoa may be selectively separated from non-motile sperm due to their natural boundary-following swimming behavior. Accordingly, highly motile spermatozoa will accumulate in the second reservoir whereas non-motile sperm accumulate in the first reservoir due to e.g. random swimming behavior and/or gravity.

Furthermore, according to the method, the second reservoir, the plurality of channels of the third layer, the separation layer, and the first reservoir are sterilized, flushed, and/or calibrated before the loading of the first reservoir with a biological sample of a mammal. This may occur e.g. by a physician, medical trained professional, user, or may have been performed during production, i.e. providing a sterile medical device in e.g. blister packaging or wrapping. Sterilization, flushing, and/or calibration may occur with e.g. ethanol, sterile and/or distilled water, and buffers, respectively.

According to the method, the second reservoir may furthermore comprise a compound that is surface bound, wherein the compound preferably comprises a compound for biological molecular signaling, preferably a chemokine, and wherein a second portion of the biological sample is selectively directed to the second reservoir. For example, the second reservoir may comprise a coating which selectively attracts motile spermatozoa, thereby causing said spermatozoa to migrate from the first reservoir to the second reservoir. Preferably, the direction and/or attraction are strong enough to facilitate such a migration yet are insignificant when compared with a force occurring during removal of the second portion of the biological sample from the second reservoir.

Preferably, the biological sample may be gently mixed with a medical grade coloring agent, which does not affect fertility and is biocompatible. Said coloring agent may e.g. be present within the first reservoir prior to loading of the biological sample and hence is mixed with the biological sample during loading. Alternatively, the biological sample may be gently mixed with a low-viscosity buffer comprising a coloring agent prior to loading of the biological sample into the first reservoir. The coloring agent may e.g. comprise colloid particles or a fluorescent component. Accordingly, not only can the loading efficacy be visually controlled, e.g. when the first layer comprises sufficient transparency, but the occurrence of undesirable convection from the first reservoir to the second reservoir may also be assessed, e.g. due to the presence of coloring agent in the removed second portion of the biological sample. The efficacy and functionality of the method may hence be assessed prior to treatment.

According to the method, the selective separation of a biological active component in the biological sample preferably occurs in a time-dependent manner, preferably during a period of time between 10 and 60 minutes, preferably 20 and 45 minutes, in particular 30 minutes. As such, this not only greatly reduces separation and/or preparation time when compared with conventional centrifugation-based methods, but simultaneously allows for an efficient separation or enrichment of the second portion, particularly spermatozoa, in the second reservoir from the first portion, particularly non-motile sperm and sediment, in the first reservoir. Furthermore, the shortened processing retains the viability of the biological sample. Although generally other period of times may be used, said times may provide optimal efficacy, even when e.g. upscaling the device for larger scale breeding purposes: the configuration of the plurality of channels may be maintained in a vertical or Z-plane. Accordingly, the separation time may be equally applicable. It may be required that the biological sample is pre-incubated, preferably at 37 degrees Celsius or alternatively at room temperature, i.e. between e.g. 20 and 25 degrees Celsius. Such pre-incubation may be necessary for e.g. liquefaction of semen, in particular spermatozoa. Without such pre-incubation, such a biological sample may be difficult to handle, impairing e.g. loading and/or aspiration.

The selective separation of a biological active component in the biological sample may furthermore be facilitated by other methods. For example, temperature, temperature gradients, or the application of an electromagnetic field may provide an increased, enriched, and/or faster separation, e.g. of highly motile spermatozoa. The application of mechanical forces such as vibration may furthermore facilitate directional movement while preventing or at least reducing the occurrence of clogging of the plurality of channels of the third layer and the fourth layer.

After the selective separation of a second portion from the biological sample, the plurality of channels of the third layer is preferably sealed at the second layer, preferably upon a flow within the second reservoir. Accordingly, the method may further prevent convection from the plurality of channels from the third layer into the second reservoir. The sealing may be achieved by e.g. valves that may either be comprised at the bottom of the second reservoir or at the top of the plurality of channels.

The second portion of the biological sample may then be removed from the second reservoir, e.g. for subsequent intra-uterine insemination. The second portion, e.g. spermatozoa, may be removed by e.g. aspiration or by injection with a fluid or air through an inlet of the second reservoir and by receiving the second portion at the outlet of the second reservoir.

Furthermore, the method may comprise that the medical device is heated to a temperature between 25 and 37 degrees Celsius prior to the loading of the first reservoir with a biological sample of a mammal and during the selective separation of a second portion in the biological sample from the first reservoir into the second reservoir. Heating to physiological conditions ensures viability. The heating may be performed by e.g. a heating unit, an incubator, or by core body temperature of a user.

The method according to the invention allows for a fast and effective enrichment of high quality sperm cells, i.e. sperm cells comprising a high motility and/or DNA integrity. Its simplicity, short duration of the selection process, and cost-effective and scalable design allow for use and implementation in either fertility clinics, fertility research laboratories, general practitioner offices, obstetrician offices, or at home, to treat male infertility. Specifically, the one-step process replaces the previous multi-stage process which involves potentially damaging forces (e.g. centrifugation) and associated risk of iatrogenic sperm injury. In addition, the short duration and passive mechanism (i.e. without fluid flow in the apparatus) minimizes oxidative stress.

Preferably, such a device and method may be used for IVF, ICSI, Intra-Uterine Insemination (IUI), and/or other ARTs and more preferably allows for a combination and/or implementation with established technologies. Ideally, such a device is furthermore transferable to non-human applications, e.g. for selecting bovine or other animal sperm for IVF or other breeding methods.

BRIEF DESCRIPTION OF THE DRAWINGS

The present disclosure will be more readily appreciated by reference to the following detailed description when being considered in connection with the accompanying drawings in which.

In the following, the invention will be explained in more detail with reference to the accompanying Figures. In the Figures, like elements are denoted by identical reference numerals and repeated description thereof may be omitted in order to avoid redundancies.

DETAILED DESCRIPTION OF PREFERRED EMBODIMENTS

Figure 1A:
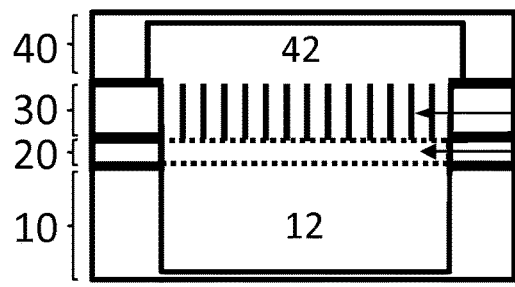
FIG. 1A is a schematic cross sectional view of a medical device for selectively separating a biological sample of a mammal, wherein the fourth layer is adjacent to the first layer.

In FIG. 1A, a medical device 1 is depicted for the selective separation of a biological sample of a mammal into a first portion and a second portion. The medical device 1 generally comprises four layers. The bottom layer 10 comprises a first reservoir 12 for receiving the biological sample. As depicted in FIG. 1, the first reservoir 12 may comprise the majority of the first layer 10 and furthermore is in fluid communication with the fourth layer 20 as indicated by the dashed line. However, other configurations, e.g. a larger first layer relative to the first reservoir, may be provided for e.g. stability and handling purposes.

The fourth layer 20 comprises a separation layer 22, which preferably comprises a porous structure, i.e. allowing compounds with a certain size or molecular mass to pass through the porous structure to the third layer 30. For example, the fourth layer may be a cellulose-based membrane, comprising pores which are large enough for spermatozoa to pass the membrane yet are small enough to prevent agglomerates or particles to enter the third layer 30.

The third layer 30 comprises a plurality of channels 32 as depicted by the plurality of vertical through lines. The channels 32 as schematically indicated here are not drawn to scale and may hence form a bottom surface area that corresponds to e.g. the size or pore sizes of the separation layer 22.

The plurality of channels 32 of the third layer 30 are furthermore in fluid communication with the second reservoir 42 of the second layer 40. Accordingly, a fluid communication is established between the first reservoir 12 of the first layer 10 and the second reservoir 42 of the second layer 40.

Figure 1B:
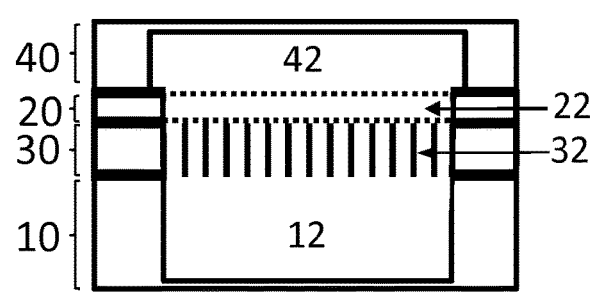
FIG. 1B is a schematic cross sectional view of a medical device for selectively separating a biological sample of a mammal, wherein the fourth layer is adjacent to the second layer.

FIG. 1B shows an alternative configuration of the medical device 1 depicted in FIG. 1A. Here, the fourth layer 20 is disposed between the third layer 30 and the second layer 40, i.e. the separation layer 22 being adjacent to the second reservoir 42 and the plurality of channels 32.

Figure 2A:
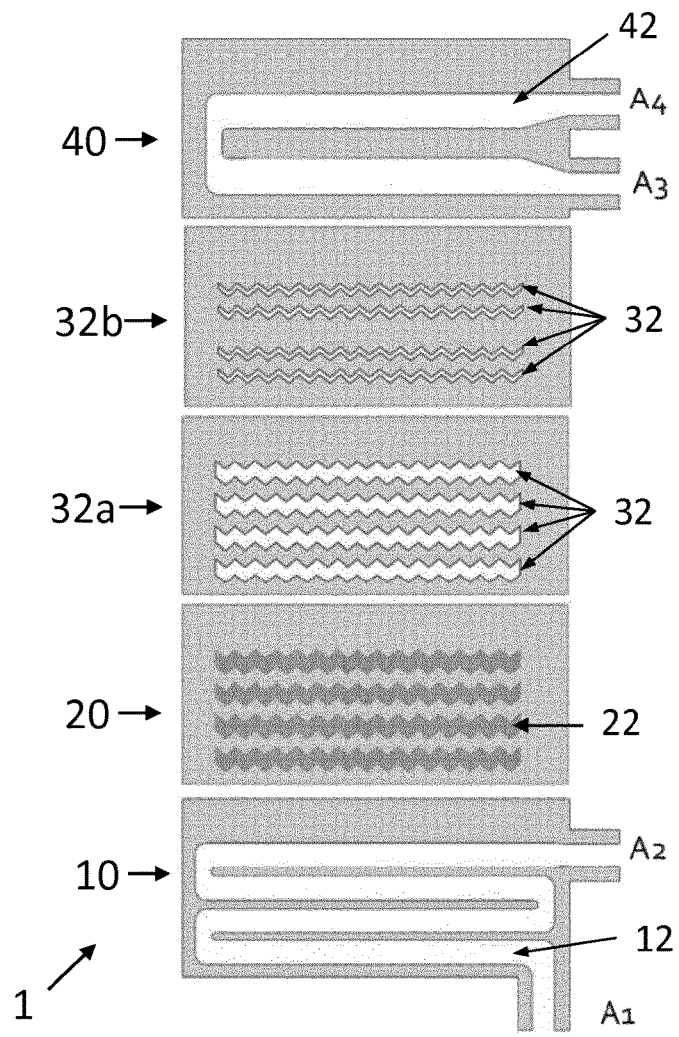
FIG. 2A is a schematic top view of another medical device for selectively separating a biological sample of a mammal at different transversal sections.
Figure 2B:
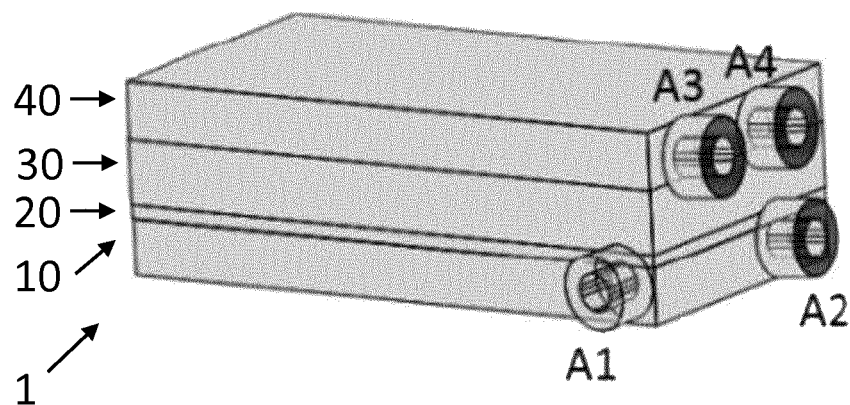
FIG. 2B is a schematic perspective view of said medical device for selectively separating a biological sample of a mammal.
Figure 2C:
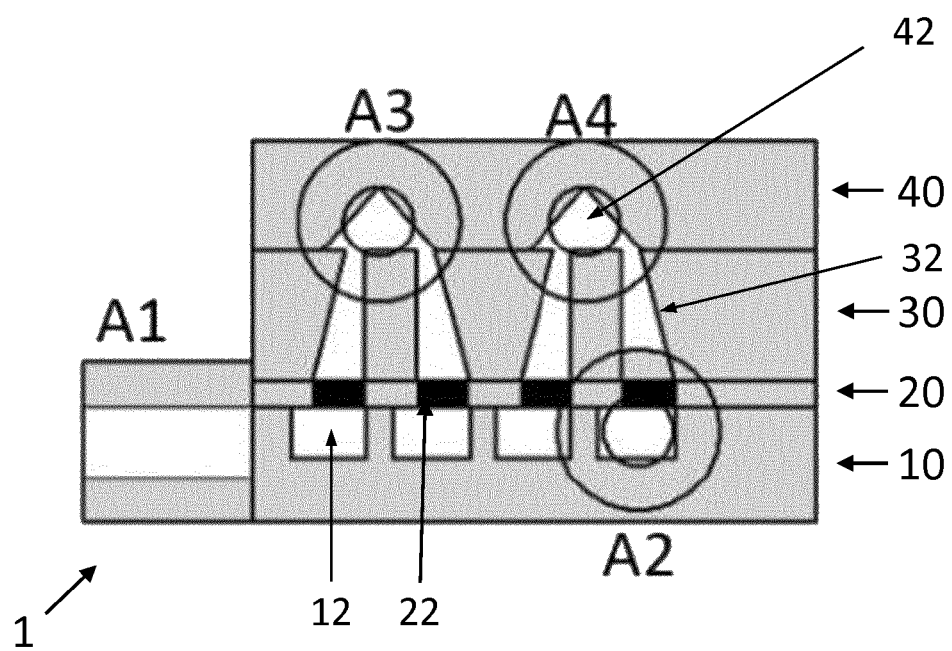
FIG. 2C is a schematic cross sectional view of said medical device for selectively separating a biological sample of a mammal.

FIGS. 2A, 2B, and 2C depict another medical device 1, wherein the plurality of channels 32 of the third layer 30 is wider towards the first layer 10, i.e. at the fourth layer 20, as depicted. Since the fourth layer 20 may also be disposed between the third layer 30 and the second layer 40, the width of the plurality of channels may be understood as to be wider at the first layer. The narrowing of the channels 32 is depicted in FIG. 2A when comparing the top side 32b of the third layer 30 with the bottom side 32a of the third layer 30. Furthermore, the plurality of channels 32 comprises a zigzag structure comprising an arrangement of edges, which at least has the advantage that e.g. the upwards wall-swimming behavior of motile spermatozoa is supported and/or direct towards the second reservoir 42.

The first reservoir 12 is furthermore depicted as a serpentine-shaped channel. Such a shape may e.g. facilitate the replacement of the buffer and/or the loading since the occurrence of bubble formation and/or "entrapment" or blocking of the first reservoir 12 by accumulating gas is prevented. Furthermore, such a shape may provide a homogenous spreading of the biological sample.

By the same token, the second reservoir 42 is depicted as a U-shaped channel. Such a shape may e.g. facilitate the removal of the second portion of the biological sample, reducing the build-up of a negative pressure, ensuring a removal of the entire portion from the second reservoir 42, and providing a laminar flow, thereby reducing convection and/or mixing of the content of the second reservoir 42 with the plurality of channels 32.

Furthermore, the medical device 1 comprises an inlet and outlet A1 and A2, and A3 and A4 for the first layer 10 and the second layer 40, respectively. The connections facilitate the loading of the biological sample and the removal of the second portion of the biological sample. The inlets and outlets A1, A2, A3, A4 are depicted to be configured as luer connectors for both handling purposes and to optimize flow characteristics, e.g. providing a laminar flow and/or reducing the occurrence of vortices, see e.g. FIG. 2B.

The narrowing of the plurality of channels 32 is furthermore depicted in FIG. 2C, forming a conical or pyramid shape. In addition, the U-shaped channel of the second reservoir 42 is depicted as a polygonal or pyramid shaped channel in a Z-plane, i.e. forming a roof-shaped structure from the bottom of the second reservoir 42. Such a shape may furthermore increase the accumulation of spermatozoa in the top of the second reservoir 42, forming a trapping system, thereby preventing highly motile spermatozoa to swim back into the plurality of channels 32, also during removal of the second portion from the second reservoir 42.

Figure 2D:
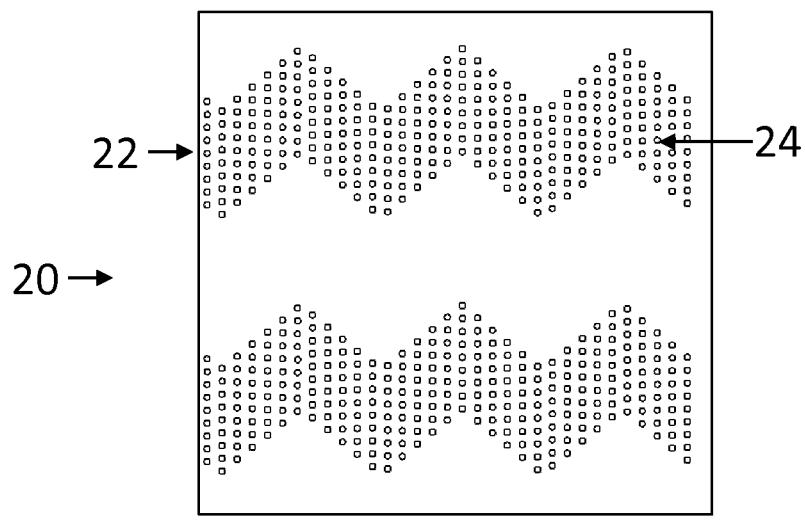
FIG. 2D is a enlarged top/bottom view of the fourth layer, wherein the separation layer comprises a multi-hole or pore structure.

The separation layer 22 preferably comprises a porous structure or multi-hole array 24 as depicted in FIG. 2D. The holes may be linear so that the top side and bottom side are symmetrical. The indicated holes are merely indicative. Accordingly, different spacing between the holes or pores may be provided and the sizes may be varied. Alternatively, the separation layer 22 may provide a continuous porous structure or multi-hole array 24 on its entire surface or at least a substantial part thereof. However, as indicated in FIG. 2D, a porous structure or multi-hole array 24 may be configured to be aligned with the plurality of channels 32 of the third layer 30 for e.g. manufacturing purposes and/or to reduce the occurrence of misalignment. Accordingly, a mask may be used to ensure optimal alignment and prevent an impaired fluid communication of the pores or holes.

Figure 3A:
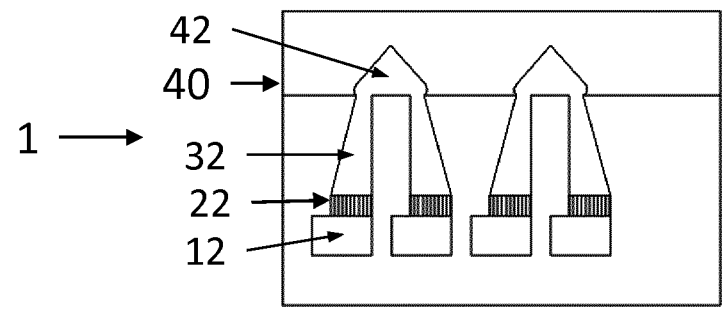
FIG. 3A-C show schematic cross sectional views of a medical device for selectively separating a biological sample of a mammal with alternative configurations of the plurality of channels and the second reservoir.
Figure 3B:
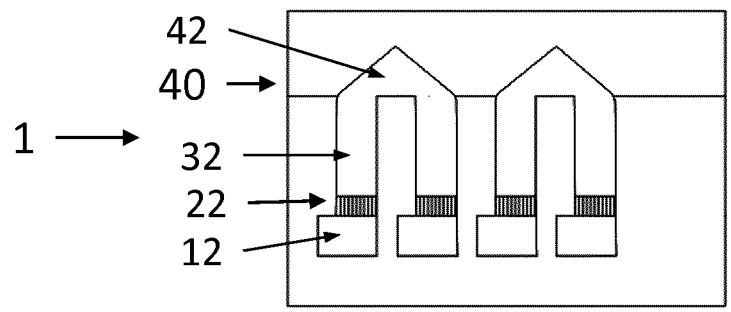
Figure 3C:
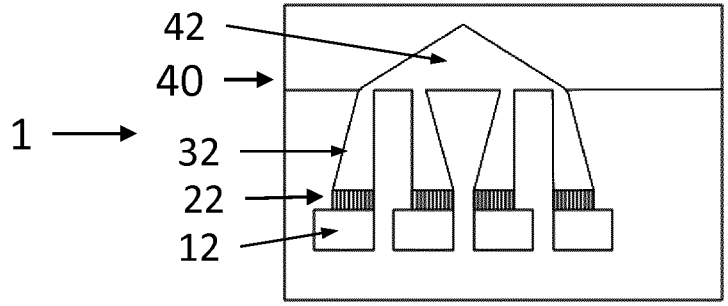

The plurality of channels 32 as well as the second reservoir 42 may have alternative configurations, as depicted in FIGS. 3A-C. The first layer 10, the third layer 30 and the fourth layer 20 are here made of a single part and form an integral part with the second layer 40. As shown in FIG. 3A, the second reservoir 42 may comprise a rounded configuration, i.e. comprising no sharp edges, at the top end of the plurality of channels 32 (compare FIG. 2A, 32b). The second reservoir 42, however, may generally comprise a polygonal shape, e.g. a pyramid shape as shown in FIGS. 3A-C, such that a corner is formed at the top of the second reservoir 42. Accordingly, highly motile spermatozoa comprising natural boundary-following swimming behavior may migrate from the first reservoir 12 through the separation layer 22 and the plurality of channels 32 to the second reservoir 42, wherein the corner at the top of the second reservoir 42 retains the spermatozoa at the top, i.e. prevents or at least impairs the spermatozoa from swimming back into the plurality of channels 32. The plurality of channels 32 is here shown to comprise a narrowing configuration along a vertical axis, i.e. being broader at the separation layer 22 than at the second reservoir 42. Again, such a configuration may facilitate both the migration of spermatozoa towards the second reservoir 42 and the retention of spermatozoa in the second reservoir 42.

Alternatively, as shown in FIG. 3B, the plurality of channels 32 may be linear, i.e. the walls not being congruent from the bottom to the top of the plurality of channels 32. Accordingly, the second reservoir 42 may comprise a larger cross sectional area, which may at least have the advantage that e.g. larger volumes may be obtained in the second reservoir 42. Here, by means of example, no rounded shape of the second reservoir 42 is indicated at the plurality of channels 32.

The second reservoir 42 may also align with more than 2 channels of the plurality of channels 32, as depicted in FIG. 3C. Accordingly, even larger volumes of the second reservoir 42 may be obtained. Such configuration may e.g. be desirable for manufacturing purposes, wherein e.g. an inlet and outlet A3, A4, are provided at either end. Accordingly, removal of spermatozoa may be facilitated. It will be understood that the described configurations only depict examples and do not limit the scope of the invention. Accordingly, other configurations and/or combinations may be provided.

Figure 4A:
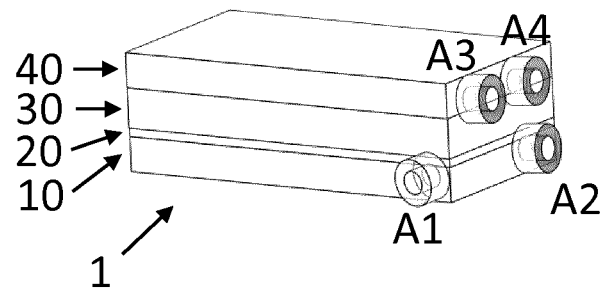
FIG. 4A-C show schematic perspective views a medical device for selectively separating a biological sample of a mammal with alternative configurations of inlets and outlets of the first and second reservoir.
Figure 4B:
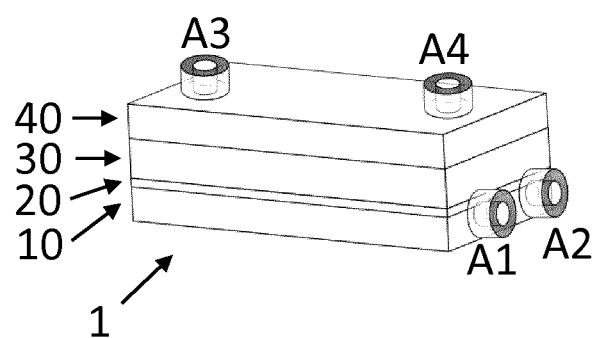
Figure 4C:
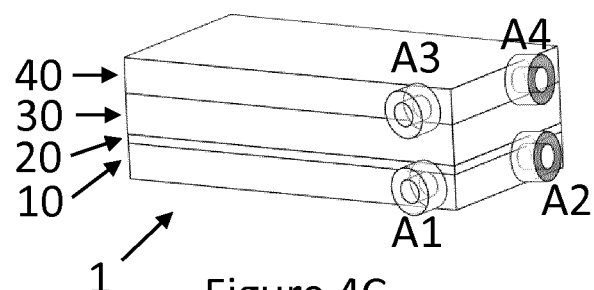

As shown in FIGS. 2B and 2C, the inlets and outlets A1, A2, A3, A4 may extend from the sides of the first layer 10 and the second layer 40. However, other configurations may be implemented, as depicted in FIGS. 4A-C. For example, as shown in FIG. 4B, the inlet and outlet A3, A4 of the second layer 40 may extend from the top of the second reservoir 42 and the second layer 40, wherein e.g. hydrostatic pressure may be used to facilitate removal of the second portion. In addition, the inlet and outlet A1, A2 of the first layer 10 may extend from only one side. This configuration at least has the advantage that the medical device 1 can be held more easily by a user, i.e. having solid and/or homogeneous sides without technical features at 4 sides. This furthermore reduces the risk of contamination. FIG. 4C shows another alternative, wherein the inlets, e.g. A1 and A3, are disposed above each other and the outlets, e.g. A2 and A4, are disposed above each other. This may reduce confusion and/or increases user-friendliness by having one side for injection or loading and one side for removal or aspiration. Furthermore, this has at least the advantage that the medical device 1 is smaller in a vertical dimension, may allow better scalability of the reservoirs 12, 42, and ensures that the medical device 1 is stackable.

The inlets and outlets A1, A2, A3, A4, may furthermore be configured as or comprise safety means. For example, they may be configured to provide a snap-fit, a luer connector, or a luer lock, known in the art. Accordingly, in the event of increased tension or pressure, such a safety means prevents a connected medical application device to be released inadvertently. Accordingly, the safety means may comprise a foolproof or poka-yoke configuration, e.g. by providing a hermaphroditic connector, an omnidirectional connector, or by providing a mechanical fit, which ensures a connection to be fail-safe. The connection may furthermore be interlocking and/or provide a clearance fit, transition fit, or interference fit. In addition, the safety means may comprise a regulating, blocking, and/or locking mechanism, which is activated when e.g. a desirable or predefined maximum pressure or flow is exceeded. Such a feature may e.g. be provided by valve arrangements or the like, as described above.

Figure 5:
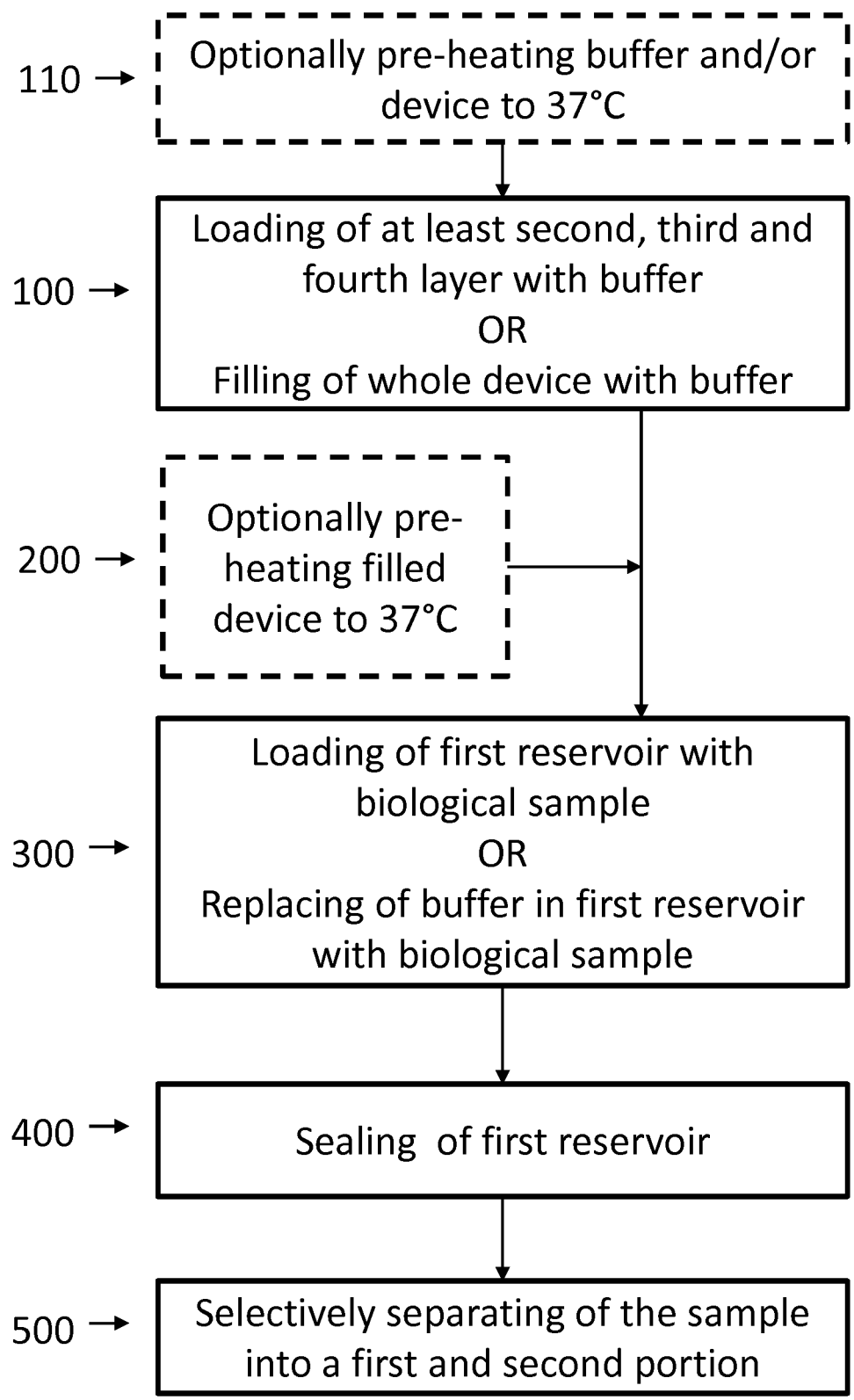
FIG. 5 is a schematic diagram of a method for selectively separating a biological sample of a mammal

FIG. 5 depicts schematically the steps of a method according to the invention for the selective separation of a biological sample of a mammal with an above described medical device. In a first step 100, at least the second reservoir 42, the separation layer 22, and the plurality of channels 32 of the third layer 30 are loaded with a buffer. The buffer may be lyophilized and already within the medical device 1, such that the injection of sterile water and mixing may be sufficient. Alternatively, a pre-mixed buffer may be injected. The injection may occur with a needle and a syringe if at least one of the layers is made of a material that allows puncture with a needle such as e.g. a biocompatible elastomer. After loading, the needle and syringe are retracted, wherein the elastomer is formed such that no fluid leaks from the first reservoir 12. However, the medical device 1 preferably comprises inlets and outlets A1, A2, A3, A4, for injection. Alternatively, the medical device 1 may be provided with a buffer by submersion into a corresponding buffer volume. Furthermore, said compartments may be flushed, incubated, and/or mixed with said buffer. In addition, the second reservoir, the plurality of channels of the third layer, the separation layer, and the first reservoir may be sterilized, flushed, and/or calibrated before the loading of said compartments with the buffer, e.g. with ethanol, sterile and/or distilled water, and buffers, respectively.

The medical device 1 may then be optionally pre-heated to preferably 37 degrees Celsius in a second, optional, step 200, prior to loading of the biological sample into the first reservoir 12. Alternatively, the medical device 1 may be kept at room temperature, e.g. between 20 and 25 degrees Celsius. However, to facilitate e.g. liquefaction of seminal plasma and for biocompatibility reasons, 37 degrees Celsius may be preferable. The buffer and/or medical device 1 may optionally also be pre-heated prior to the loading of the respective layers (10; 20; 30; 40) of the medical device 1 with buffer, step 110. Accordingly, the medical device 1 may also be retained at room temperature, i.e. not heated, before and/or after loading of the medical device 1 with buffer.

By the same token, the biological sample may be pre-heated and/or incubated to preferably 37 degrees Celsius prior to loading of the first reservoir 12. This at least has the advantage that a liquefaction of e.g. semen may occur, the handling of the biological sample may be facilitated, and/or may provide better biocompatibility or viability of the biological sample. For example, a pre-incubation of the biological sample at 37 degrees Celsius between 1 and 60 minutes, preferably between 10 and 30 minutes, may be preferable.

The first reservoir is then loaded with a biological sample of a mammal in a third step 300, wherein the second reservoir 42 is fluidly sealed. The loading of the first reservoir 12 with the biological sample may, if present, replace a buffer in the first reservoir 12. Such loading may e.g. occur with a syringe and a corresponding inlet or outlet A1, A2 of the first reservoir 12 by e.g. injection of a fluid or air. However, the first reservoir 12 and the first layer 10 may be made of a material that allows puncture with a needle such as e.g. a biocompatible elastomer. Accordingly, the loading may alternatively occur with a needle and a syringe, which may be preferable for handling or hygiene purposes. After loading, the needle and syringe are retracted, wherein the elastomer is formed such that no fluid leaks from the first reservoir 12. However, for safety reasons, the use of sharp needles may be not preferable. Furthermore, needles may only be used after sufficient liquefaction of seminal plasma for handling purposes. Appropriate needle dimensions may hence be provided to reduce safety issues, facilitate handling, and/or reduce adverse effects on the quality and/or DNA integrity of spermatozoa.

The first reservoir is accordingly fluidly sealed in a fourth step 400, without establishing a pressure gradient between the first reservoir 12 and the second reservoir 42. The prevention of a pressure gradient and/or convection may e.g. be accomplished by the configuration of the plurality of channels 32 and/or the configuration of the separation layer 22.

The biological sample is then selectively separated between the first reservoir 12 and the second reservoir 42 into a first portion and a second portion in a fifth step 500. The selective separation preferably occurs at 37 degrees Celsius, e.g. by heating, but may alternatively occur at room temperature. Furthermore, the selective separation preferably occurs due to a combination of directional motility and gravitational force. For example, spermatozoa may be selectively separated from non-motile sperm due to their natural wall swimming character. Preferably, the plurality of channels 32 of the third layer 30 are thereby substantially oriented towards or aligned with a plane of gravitational force. This prevents or at least reduces the undesirable accumulation of non-motile sperm cells, sediment, and particles into the plurality of channels 32 of the third layer 30. This not only prevents the occurrence of a potential block, impairing movement of highly motile spermatozoa towards the second reservoir 42, but also increases purity and enrichment of motile spermatozoa with high quality DNA at the top of the second reservoir 42.

Figure 6:
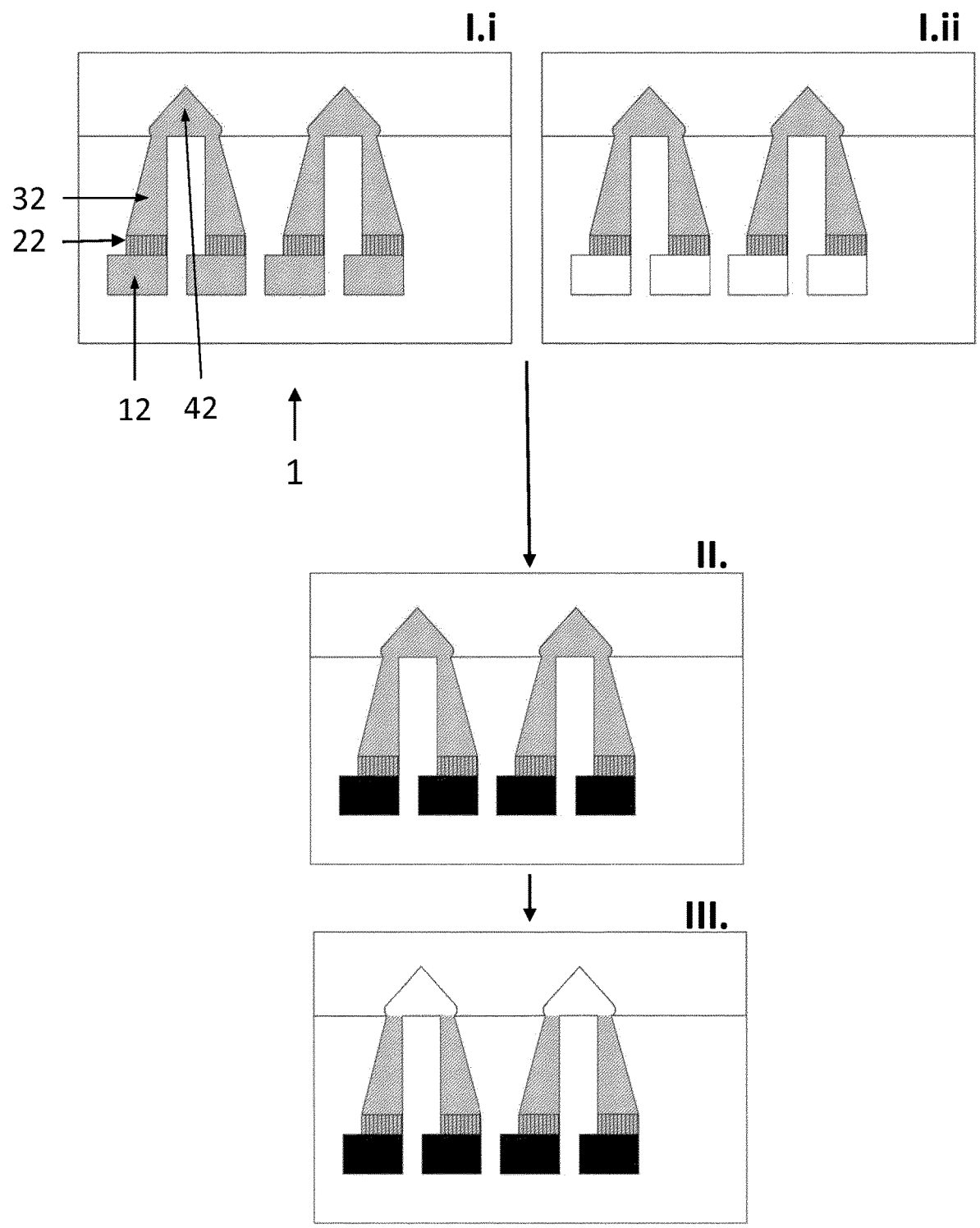
FIG. 6 shows the schematic cross sectional view of FIG. 3A to indicate a method according to the invention.

FIG. 6 shows an example of the different stages of the method according to the invention. By means of example, the medical device 1 is depicted as a cross sectional side view similar to the embodiment shown in FIG. 3A. As indicated in step I.i, the first reservoir 12, the second reservoir 42, the plurality of channels 32 and separation layer 22 therebetween, may be filled with a buffer (grey). Alternatively, the first reservoir 12 may remain empty, as indicated by step I. ii (white). Both steps hence resemble the method step 100, as depicted in e.g. FIG. 5.

Step II. depicts how the first reservoir 12 of the medical device 1 may then be filled with a biological sample (black), similar to the method step 300 shown in FIG. 5. The biological sample (black) may hence either replace the buffer (grey) or fill the first reservoir, according to step I.i and I.ii, respectively. Alternatively, the first reservoir 12 of may be filled with the biological sample before the filling of the second reservoir 42, plurality of channels 32, and the separation layer 22, i.e. step I.ii would follow after filling the first reservoir 12 with the biological sample. After fluidly sealing all compartments, the separation of the second portion into the second reservoir 42 may then take place (not shown).

Step III. shows how a second portion (not shown) may be removed from the second reservoir 42 after the separation of the second portion from the biological sample into the second reservoir 42. As indicated, the second portion is removed together with the buffer, leaving the second reservoir 42 empty (white) or at least removing a substantial volume from the second reservoir 42. As described above, the removal may occur according to various alternatives, e.g. by injecting air or injecting a fluid at an inlet and accordingly receiving the second portion in the buffer at the outlet of the second reservoir 42. Alternatively, the second portion may be obtained by e.g. aspiration or suction.

Figure 7:
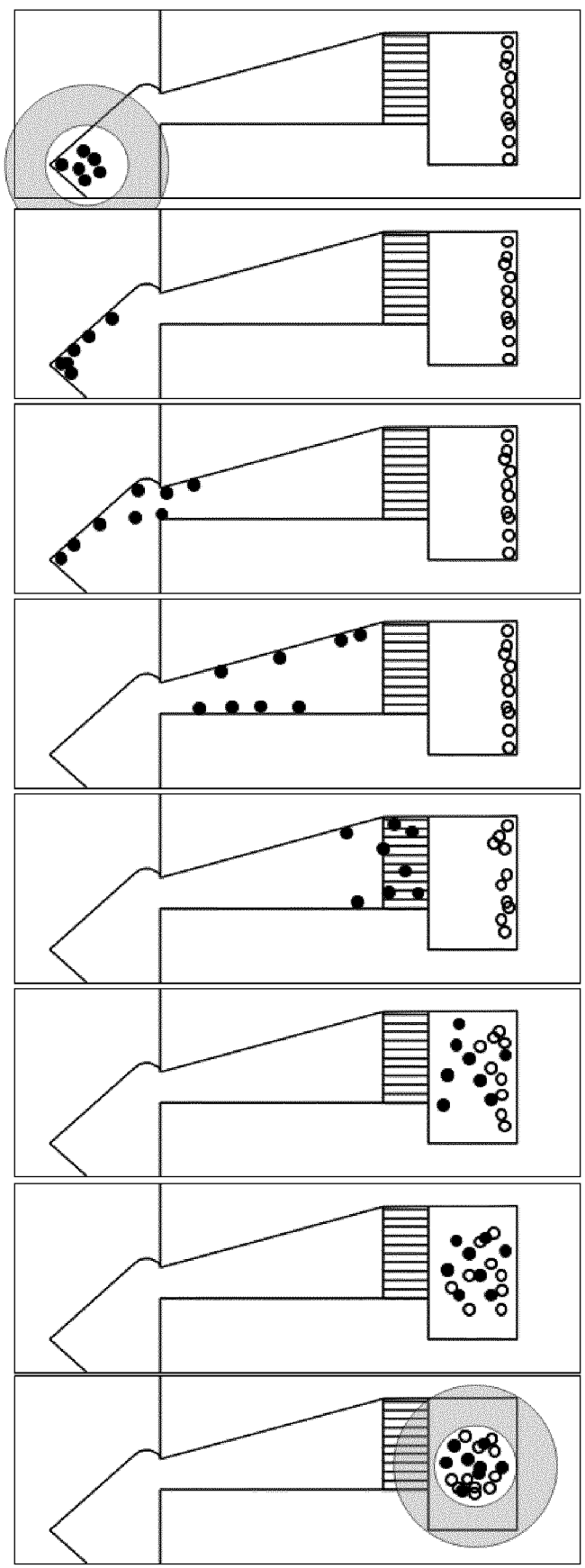
FIG. 7 schematically shows the separation of a second portion of the biological sample from the first reservoir into the second reservoir.

The separation of the second portion of the biological sample between the first reservoir 12 and the second reservoir 42 is schematically depicted in FIG. 7, according to, by means of example, the medical device 1 of FIG. 3A. After loading of the first reservoir 12 at an inlet (A1, A2, A3, A4), depicted in I., the biological sample is provided in the first reservoir 12. The biological sample is here depicted as a mixture of circles (empty) and dots (black) representing a first portion and second portion, respectively. Accordingly, the second portion may e.g. comprise high quality spermatozoa while the first portion may e.g. comprise other cells, dead sperm cells and/or seminal plasma.

After distribution, the circles, e.g. dead cells, settle at the bottom of the reservoir 12 due to e.g. gravitational force and/or random motion. However, the dots, e.g. high quality spermatozoa, migrate towards the second reservoir 42 due to a combination of their natural boundary-following and upward swimming behavior. Accordingly, the dots pass through the separation layer 22 and enter the plurality of channels 32, preferring to follow edges and/or walls in contrast to random swimming behavior of e.g. low quality spermatozoa. The narrowing of the plurality of channels 32 at the top, i.e. at the second reservoir 42, as shown in FIG. 7, not only directs spermatozoa but furthermore prevents or at least impairs a back-swimming after the dots reach the second reservoir.

The configuration of the second reservoir 42 at the top is chosen to retain the majority of high quality spermatozoa at the top of the reservoir 42. For example, the provision of edges, as depicted in e.g. FIG. 7, facilitates the accumulation of high quality spermatozoa. Towards the end of step II., the second portion, e.g. spermatozoa, may hence be retrieved from the second reservoir 42, e.g. at an outlet of the second reservoir 42, as depicted in FIG. 7. Accordingly, the medical device 1 allows for an efficient separation of the second portion of the biological sample between the first reservoir 12 and the second reservoir 42 due to a combination of the configuration of the medical device 1, biological activity of the second portion, e.g. natural boundary-following and upward swimming behavior, and/or gravity.

Figure 8A:
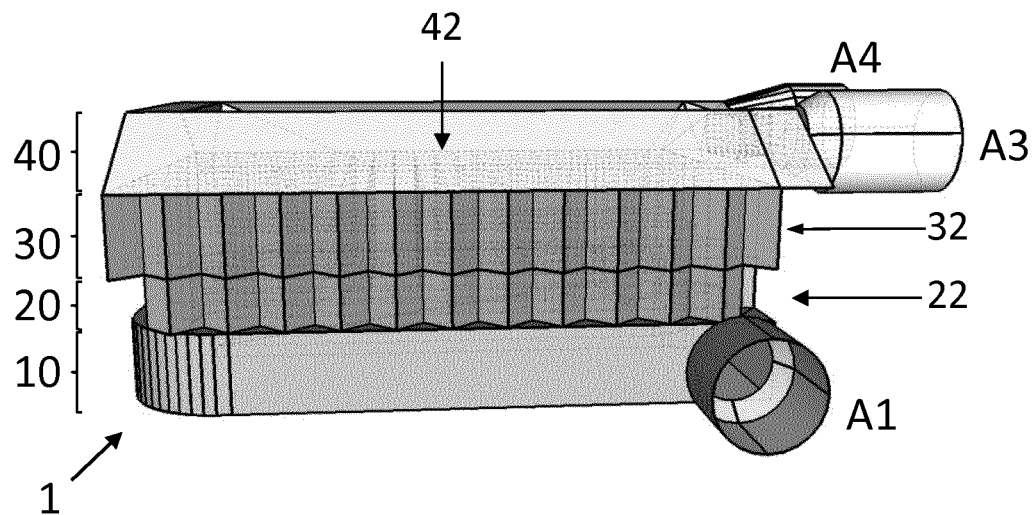
FIG. 8A shows a schematic perspective view of a medical device for selectively separating a biological sample of a mammal as seen from one side of the medical device, wherein the separation layer comprises openings with triangular geometries.

The separation layer 22 of the fourth layer 20 may comprise alternative configurations. Accordingly, instead of or as a configuration of e.g. a porous structure or multi-hole array, said layer may comprise triangular geometries as depicted in FIGS. 8A-F. FIG. 8A shows a side view of such a configuration, wherein the separation layer 22 is interposed between the first layer 10 and the third layer 30. Although both the third layer 30 and fourth layer 20 are depicted to comprise an outer zig-zag structure, other configurations such as a continuous, smooth and/or homogenous outer wall may be provided in alternative embodiments. However, a zig-zag structure may at least have the advantage that a better grip or holding of the medical device 1 may be provided while simultaneously facilitating a stronger structural support.

Figure 8B:
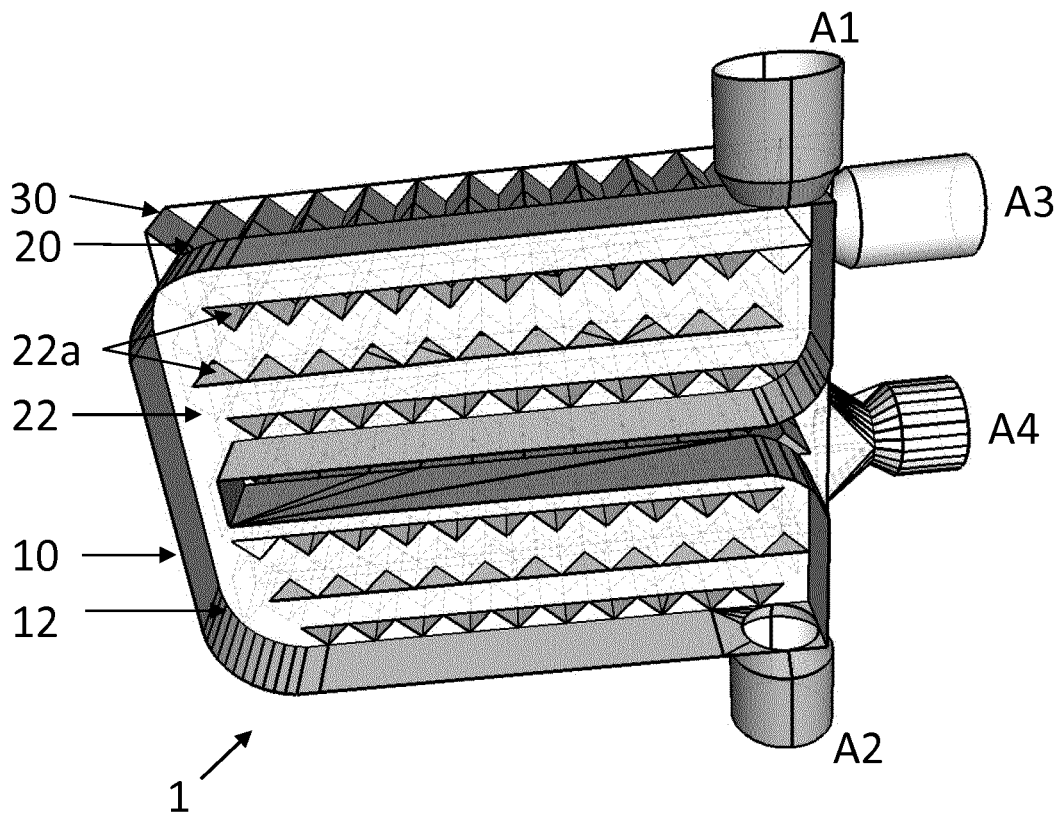
FIG. 8B shows a schematic perspective view of said medical device for selectively separating a biological sample of a mammal as seen from the bottom of said medical device, the bottom wall of the first layer being removed.
Figure 8C:
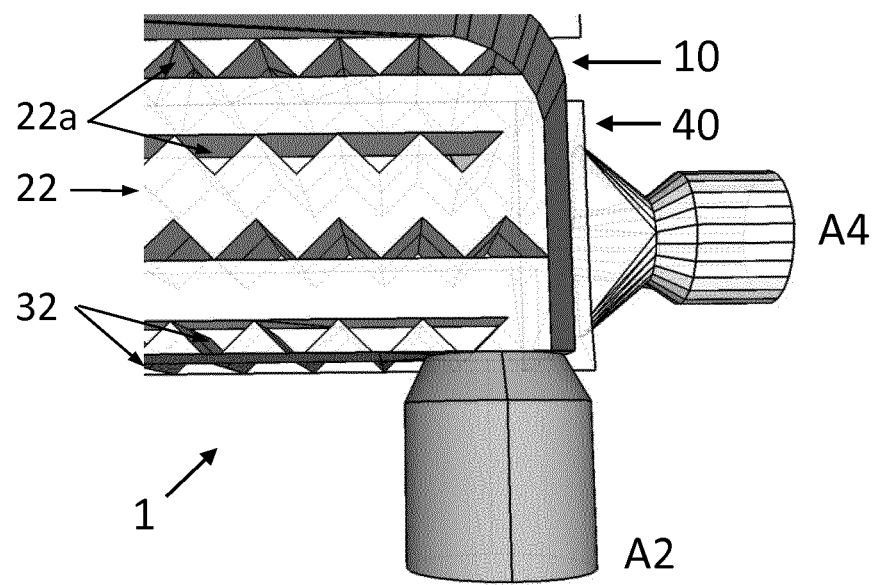
FIG. 8C shows a blowup schematic bottom view of said medical device for selectively separating a biological sample of a mammal, the bottom wall of the first layer being removed.
Figure 8D:
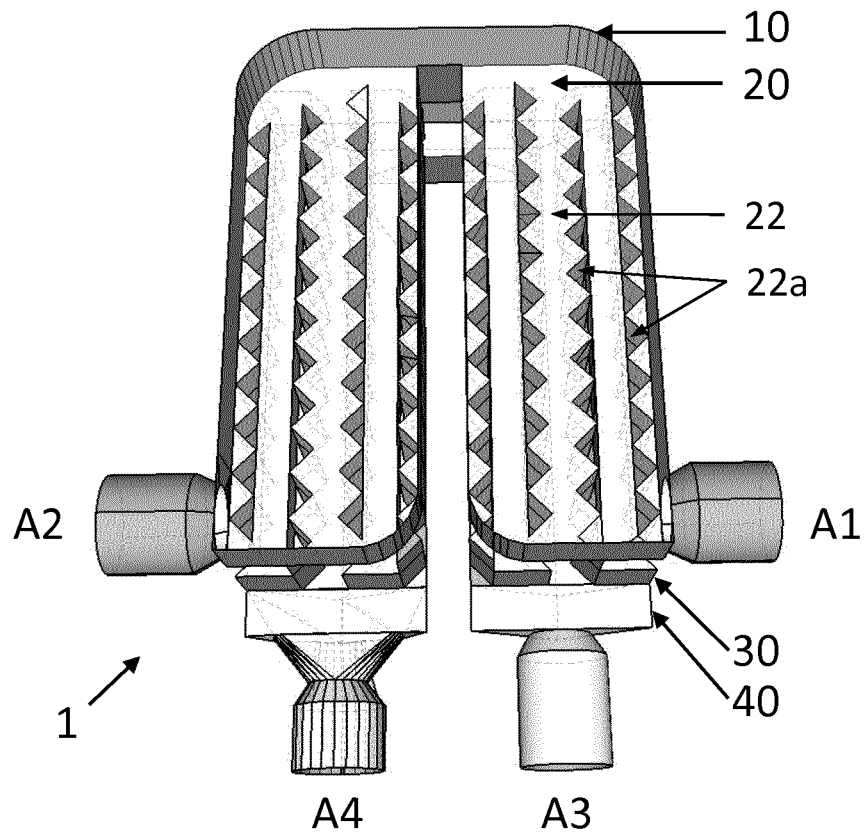
FIG. 8D shows another schematic perspective view of said medical device for selectively separating a biological sample of a mammal as seen from the bottom of said medical device, the bottom wall of the first layer being removed.
Figure 8E:
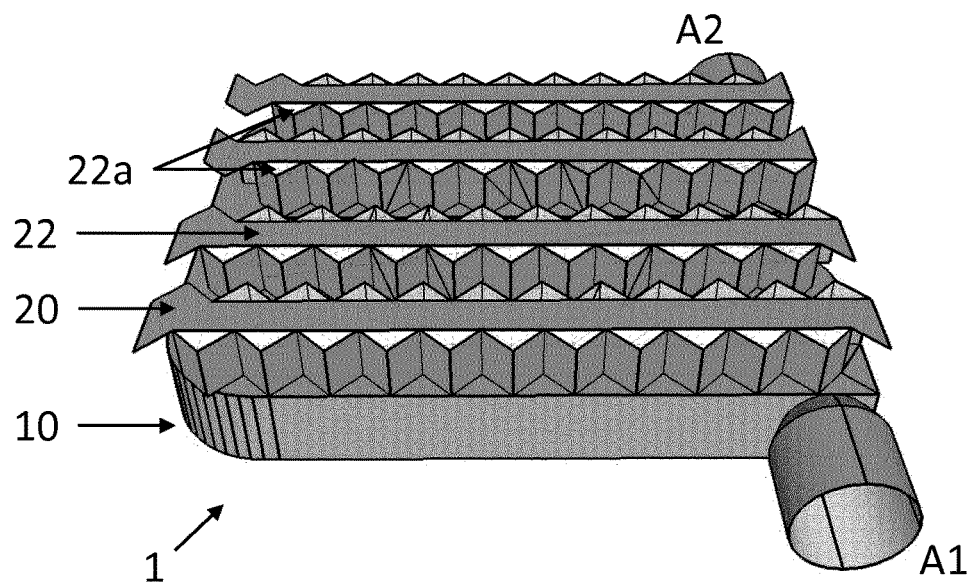
FIG. 8E shows a schematic perspective view of said medical device for selectively separating a biological sample of a mammal, wherein the second and third layer are removed.
Figure 8F:
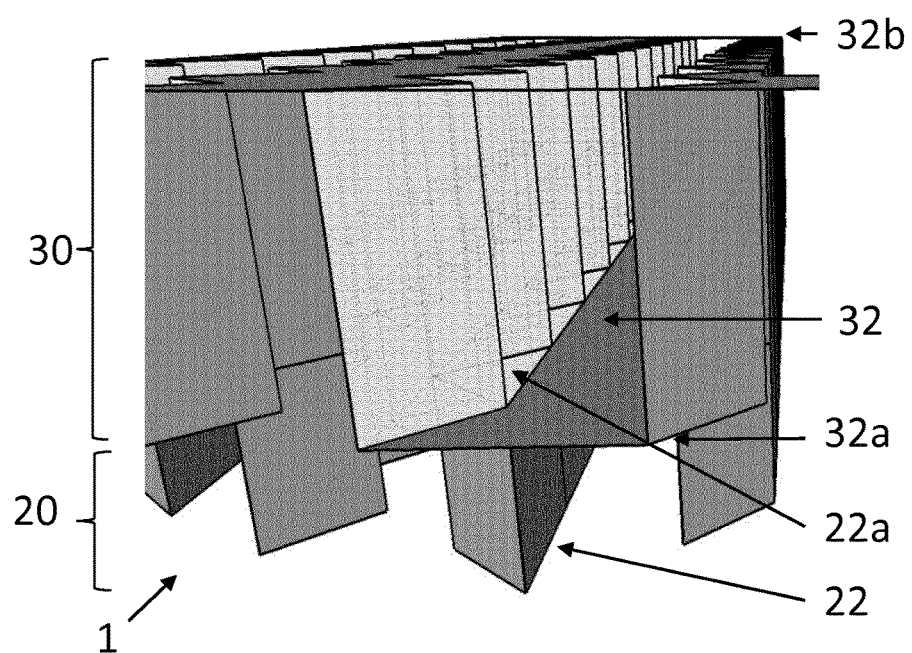
FIG. 8F shows a schematic perspective view of said medical device for selectively separating a biological sample of a mammal at a cross section, wherein the first and second layer are removed.

The triangular geometries provide openings 22a that establish a fluid communication between the reservoir 12 of the first layer 10 and the plurality of channels 32 of the third layer 30, as generally depicted in FIGS. 8B-8F. The openings 22a are shown to be linear so that the top side and bottom side are symmetrical. However, alternative configurations, e.g. wherein the openings 22a are congruent from the first layer 10 towards the third layer 30, may be provided. Preferably, at least one corner of each opening 22a is an extension of the triangular wall structure in the plurality of channels, such that the openings 22a are aligned, preferably fully aligned with the plurality of channels 32 of the third layer 30, as best depicted in e.g. FIGS. 8D and 8F. The size and the number of the openings 22a as well as the spacing between said openings are merely indicative, such that other patterns including e.g. smaller and/or more triangles may be provided. Whereas FIGS. 8E and 8F depict the openings 22a of the separation layer 22 as an extracted view, FIGS. 8B-8D depict said openings in a solid depiction of the separation layer 22.

The at least partial alignment of the openings 22a with the plurality of channels 32 of the third layer 30 has at least the advantage that manufacturing of the device is facilitated and is possible using e.g. 3D printing with even low density printers. This allows for cheap prototyping and manufacturing and doesn't require any assembly steps since the device may be printed in one piece. Also, by providing corners that sperm can swim in, the triangular opening provide immediate guidance for sperm after leaving the first reservoir. Accordingly, the separation layer 22 may facilitate the selective separation of a biological sample of a mammal, in particular of sperm.

Although the size and geometry of the openings 22a may vary, said openings 22a preferably comprise dimensions between 0.5 mm×0.5 mm×0.5 mm and 5 mm×5 mm×5 mm, preferably between 1 mm×1 mm×1 mm and 3 mm×3 mm×3 mm, more preferably 1.4 mm×1.4 mm×2 mm, while comprising a height substantially corresponding to a height of the separation layer 22 in the range of 0.5 to 5 mm, preferably between 1 and 3 mm, more preferably 2 mm.

The embodiment as depicted in FIGS. 8A-F furthermore comprises a first layer 10, wherein the corners of said layer comprise a rounded shape. Accordingly, said shape may substantially correspond to the shape of the first reservoir 12. The rounded shape at least has the advantage that flow performance of the biological sample is improved when loaded into said first reservoir 12 through one of the inlets A1, A2. Furthermore, the rounded corners may increase the usability or handling of the medical device 1 by a user. However, other shapes including rectangular and/or solid shapes may be implemented such that the outer wall of the first layer 10 may enclose or receive the first reservoir 12, e.g. the bottom of said reservoir.

By the same token, the plurality of channels 32 of the third layer 30 are depicted in FIGS. 8A-F to not comprise a congruent, narrowing, or pyramid shape, i.e. not comprising a shape that is wider at the fourth layer 20 than at the second layer 40. However, such configurations as well as other configurations, as described in the above, may also be provided.

Furthermore, the second layer 40 is depicted comprising the second reservoir 42 with a roof-shaped configuration. This at least has the advantage that e.g. sperm may follow the boundaries and corners provided by said roof-shaped configuration and is hence retained or at least substantially prevented from leaving the second reservoir 42 after entering said reservoir. However, other configurations of the second reservoir 42, as described in the above, may be provided.

The orientation of the inlets and outlets A1, A2, A3, A4 is depicted in FIGS. 8A-D such that the inlet and outlet A1, A2 of the first layer 10 or reservoir 12 are oriented in opposite directions in one orientation plane, whereas the inlet and outlet A3, A4 of the second layer 40 or reservoir 42 are oriented in the same direction, i.e. are orientated in parallel in another orientation plane. All inlets and outlets are furthermore arranged at one end or side of the medical device 1. This configuration at least has the advantage that handling of the medical device 1 may be facilitated, leaving enough space to hold the medical device 1, and furthermore reduces the risk of confusion for a user by performing different steps, e.g. the loading of the first reservoir 12 and the removal of a second portion from the second reservoir 42, in different planes of orientation. However, other orientations of said inlets and outlets may be provided, as described above and/or depicted in e.g. FIGS. 4A-C.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS

1 Medical device
10 First layer
12 First reservoir
20 Fourth layer
22 Separation layer
22a Openings
24 Multi-hole array or porous structure
30 Third layer
32 Plurality of channels
32a Bottom of third layer
32b Top of third layer
40 Second layer
42 Second reservoir
100 First method step
200 Second method step
300 Third method step
400 Fourth method step
500 Fifth method step
A1 Inlet or outlet of first layer/reservoir
A2 Inlet or outlet of first layer/reservoir
A3 Inlet or outlet of second layer/reservoir
A4 Inlet or outlet of second layer/reservoir

The invention claimed is:

1. A medical device for selective separation of a biological sample of a mammal into portions, comprising:
   a first layer comprising a first reservoir with a fluid biological sample contained therein, the fluid biological sample including at least a first portion of a fluid, and a motile component;
   a second layer comprising a second reservoir containing a second portion of the fluid and receiving at least part of the motile component of the fluid biological sample from the first reservoir;
   a third layer between the first layer and the second layer, wherein the third layer comprises a plurality of channels configured to provide a fluid communication between the first reservoir and the second reservoir, wherein the plurality of channels contain a third portion of the fluid; and
   a fourth layer positioned between one of the first layer and the third layer or the second layer and the third layer, the fourth layer comprising a separation layer, wherein at least the third and fourth layers are configured to selectively separate the at least part of the motile component from the first reservoir into the second reservoir
   wherein the positions of the first, second, third and fourth layers are such that during use, a pressure difference defined from the second reservoir to the first reservoir is zero.

2. The medical device according to claim 1, wherein the fourth layer is between the first layer and the third layer, and comprises a porous structure located proximate a top surface of the first reservoir, wherein the porous structure comprises one of: a multi-hole array with triangular geometries or openings defining a plurality of pores coinciding with a plurality of openings of the plurality channels of the third layer at the fourth layer.

3. The medical device according to claim 2, wherein the plurality of openings are sized and shaped to minimize the occurrence of convection and/or pressure difference within and/or between at least the second and third layers, and wherein each of the plurality of openings has a triangular geometry.

4. The medical device according to claim 1, wherein the fluid biological sample comprises semen, comprising the motile component, which is sperm or spermatozoa.

5. The medical device according to claim 1, wherein the plurality of channels of the third layer have an angular orientation relative to the first layer and/or second layer of at least 60 degrees or an angular orientation perpendicular to the first layer and/or second layer.

6. The medical device according to claim 1, wherein the first layer, the second layer, the third layer, and the fourth layer are stacked on one another such that the second layer is on top of the first layer, the third layer, and the fourth layer and the first reservoir is formed as a channel extending in an orientation corresponding to a plane of the first layer, the plurality of channels of the third layer being configured for directing movement of the at least part of the motile component of the fluid biological sample from the first reservoir to the second reservoir.

7. The medical device according to claim 6, wherein the first reservoir that is formed as a channel is non-linear and/or defines a meandering, sinuous, helical, pedigree, circular, ellipse, U-shaped, serpentine-shaped, and/or zig-zag path having no sharp edges.

8. The medical device according to claim 1, wherein each channel of the third layer comprises a surface structure that promotes and/or supports motility of the motile component of the fluid biological sample.

9. The medical device according to claim 1, wherein each of the plurality of channels of the third layer is at least one of: non-linear and/or comprises an arrangement of edges.

10. The medical device according to claim 1, wherein each of the plurality of channels of the third layer has a width that is larger at the first layer than at the second layer.

11. The medical device according to claim 1, wherein each of the plurality of channels of the third layer define a meandering, sinuous, helical, and/or zig-zag path.

12. The medical device according to claim 1, wherein the second reservoir comprises at least one side, bottom, and/or top surface having a rounded, cylindrical, semicircular, conical, U-shaped, and/or polygonal shape and the at least one side, bottom, and top surface is shaped to provide a retaining structure for the at least part of the motile component of the fluid biological sample, to prevent convection during flow of the at least part of the motile component of the fluid biological sample, and/or to prevent turbulence during flow of the at least part of the motile component of the fluid biological sample.

13. The medical device according to claim 1, wherein at least one of the first reservoir and/or the second reservoir is configured to minimize convection, fluid resistance, and/or turbulent flow when the fluid biological sample flows through the medical device.

14. The medical device according to claim 1, wherein the separation layer further comprises a porous structure comprising a plurality of openings each having a pore size between 20 and 500 p.m.

15. The medical device according to claim 1, wherein the first reservoir comprises a volume between 0.5 and 5 mL and the second reservoir comprises volume between 100 pL and 1 mL,
wherein each of the plurality of channels comprises a length between 2 and 15 mm, and/or the fourth layer comprises a length between 100 micrometers and 1 mm.

16. The medical device according to claim 1, wherein the first reservoir and the second reservoir each comprise an inlet and an outlet, wherein at least one inlet and/or one outlet can be selectively opened and/or closed, wherein an inlet and/or outlet of each of the first reservoir and the second reservoir is adapted to connect and/or receive a second medical device, and/or an inlet and/or outlet of each of the first reservoir and the second reservoir is configured to minimize convection, fluid resistance, and/or turbulent flow when the fluid biological sample is removed from the second reservoir.

17. The medical device according to claim 1, wherein at least one of the first reservoir and/or the second reservoir comprises a valve arrangement, wherein the valve arrangement minimizes the occurrence of gas accumulation in the at least one of the first and/or second reservoir.

18. The medical device according to claim 17, wherein the valve arrangement further comprises a flow constriction means to control a flow of the fluid biological sample with the at least one of the first reservoir and/or the second reservoir.

19. The medical device according to claim 1, wherein the plurality of channels of the third layer comprises a closing means for sealing of the third layer at least one of the first layer and/or the second layer, the closing means being configured to prevent convection of the fluid from the plurality of channels of the third layer into the second reservoir, and wherein the closing means comprises one of: a microfluidic valve, a sealable membrane, a solenoid valve, and/or diaphragm valve and is configured to be selectively closed in at least one flow direction.

20. The medical device according to claim 1, wherein the first layer, the second layer, the third layer, and the fourth layer are unitarily formed, and wherein the medical device is portable and usable as a home-care product.

21. The medical device according to claim 1, wherein the fourth layer comprises a porous structure located proximate the plurality of channels of the third layer, wherein the porous structure comprises one of a multi-hole array with triangular geometries or openings defining a plurality of pores coinciding with a plurality of openings of the plurality channels of the third layer at the fourth layer.

22. A system for the selective separation of a motile component of a biological sample of a mammal, comprising:
a fluid biological sample including at least a first portion of a fluid and a motile component;
at least one medical device according to claim 1; comprising:
the first reservoir for receiving the fluid biological sample and for retaining at least the fluid of the fluid biological sample;
the second reservoir for receiving the at least part of the motile component of the fluid biological sample from the first reservoir;
at least one medical application device for loading the first reservoir of the at least one medical device with the fluid biological sample; and
a second medical application device for removing the at least part of the motile component of the fluid biological sample from the second reservoir of the at least one medical device and configured to administer the at least part of the motile component of the fluid biological sample to a patient.

23. The system according to claim 22, further comprising a heating unit for maintaining the system at a temperature, between 25 and 37 degrees Celsius.

24. A method for the selective separation of a fluid biological sample of a mammal with a medical device, comprising the steps of:
providing a medical device according to claim 1 comprising the first layer comprising the first reservoir for receiving the fluid biological sample and for retaining the fluid biological sample, the second layer comprising the second reservoir for receiving at least a part of the motile component of the fluid biological sample, the third layer between the first layer and the second layer, wherein the third layer comprises the plurality of channels configured to provide a fluid communication between the first reservoir and the second reservoir, and the fourth layer positioned between one of the first layer and the third layer or the second layer and the third layer, and comprising the separation layer, wherein at least the third and fourth layer are configured to selectively separate the at least part of the motile component of the fluid biological sample from the first reservoir to the second reservoir;
preparing at least the second reservoir, the separation layer, and the plurality of channels of the third layer with a buffer;
loading the first reservoir with the fluid biological sample,
fluidly sealing the first reservoir without establishing a pressure difference between the first reservoir and the second reservoir; and
selectively separating the motile component of the fluid biological sample from the first reservoir to the second reservoir.

25. The method according to claim 24, wherein the second reservoir comprises a surface-bound compound for selectively directing the motile component of the fluid biological sample to the second reservoir, and wherein the compound comprises a compound for biological molecular signaling.

26. The method according to claim 24, further comprising the step of adjusting a plane of the medical device to prevent the accumulation of gas in at least the first reservoir during the loading of the first reservoir with the fluid biological sample.

27. The method according to claim 24, wherein the step of selectively separating the fluid biological sample occurs over a period of time having a duration ranging from 10 minutes to 60 minutes, and/or wherein the medical device is heated to a temperature ranging from 25 degrees to 37 degrees Celsius prior to the loading of the first reservoir with the fluid biological sample and during the selective separating of the at least part of the motile component of the fluid biological sample.

28. The method according to claim 24, wherein the preparing step further comprises one of loading, flushing, incubating, and/or mixing at least the second reservoir, the separation layer, and the plurality of channels of the third layer with a buffer.

* * * * *